(12) United States Patent
Chen et al.

(10) Patent No.: US 10,519,500 B2
(45) Date of Patent: Dec. 31, 2019

(54) CRYSTALLINE COPPER-BASED COORDINATION POLYMERS AND THEIR USE

(71) Applicants: Southern Medical University, Guangzhou (CN); Macau University of Science and Technology, Taipa (MO)

(72) Inventors: Jin-Xiang Chen, Guangzhou (CN); Bao-Ping Xie, Guangzhou (CN); Gui-Hua Qiu, Guangzhou (CN); Pei-Pei Hu, Guangzhou (CN); Zhen Liang, Guangzhou (CN); Ye-Mei Liang, Guangzhou (CN); Bin Sun, Guangzhou (CN); Li-Ping Bai, Taipa (MO); Zhi-Hong Jiang, Taipa (MO)

(73) Assignees: MACAU UNIVERSITY OF SCIENCE AND TECHNOLOGY, Taipa (MO); SOUTHERN MEDICAL UNIVERSITY, Guangzhou (CN)

( * ) Notice: Subject to any disclaimer, the term of this patent is extended or adjusted under 35 U.S.C. 154(b) by 157 days.

(21) Appl. No.: 15/600,957

(22) Filed: May 22, 2017

(65) Prior Publication Data
US 2018/0334713 A1    Nov. 22, 2018

(51) Int. Cl.
   C12Q 1/68        (2018.01)
   C08G 79/00       (2006.01)
   C12Q 1/6876      (2018.01)

(52) U.S. Cl.
   CPC ........... *C12Q 1/6876* (2013.01); *C08G 79/00* (2013.01)

(58) Field of Classification Search
   CPC .............................. C12Q 1/6876; C08G 79/00
   USPC ................................................. 546/2; 435/6.1
   See application file for complete search history.

(56) References Cited

PUBLICATIONS

X. Zhu, H. Zheng, X. Wei, Z. Lin, L. Guo, B. Qiu, G. Chen, Metal organic framework (MOF): a novel sensing platform for biomolecules, Chem. Commun. 49 (2013) 1276-1278.
H.T. Zhang, J.W. Zhang, G. Huang, Z.Y. Du, H.L. Jiang, An amine-functionalized metal organic framework as a sensing platform for DNA detection, Chem. Commun. 50 (2014) 12069-12072.
T. Ye, Y.F. Liu, M. Luo, X. Xiang, X.H. Ji, G.H. Zhou, Z.K. He, Metal-organic framework-based molecular beacons for multiplexed DNA detection by synchronous fluorescence analysis, Analyst 139 (2014) 1721-1725.
D.S. Xiang, A.H. Zheng, M. Luo, X.H. JI, Z.K. HE, Graphene oxide and molecular beacons-based multiplexed DNA detection by synchronous fluorescence analysis, Science China 56 (2013) 380-386.
A.L. Spek, Platon Squeeze: a tool for the calculation of the disordered solvent contribution to the calculated structure factors, Acta Crystallogr. C Struct. Chem. 71 (2015) 9-18.
S.P. Yang, S.R. Chen, S.W. Liu, X.Y. Tang, L. Qin, G.H. Qiu, J.X. Chen, W.H. Chen, Platforms formed from a three-dimensional Cu-based zwitterionic metal-organic framework and probe ss-DNA: Selective fluorescent iosensors for human immunodeficiency virus 1 ds-DNA and sudan virus RNA sequences, Anal. Chem. 87 (2015) 12206-12214.
L. Qin, L.X. Lin, Z.P. Fang, S.P. Yang, G.H. Qiu, J.X. Chen, W.H. Chen. A water-stable metal-organic framework of a zwitterionic carboxylate with dysprosium: a sensing platform for Ebolavirus RNA sequences, Chem. Commun. 52 (2016) 132-135.
H.Q. Zhao, G.H. Qiu, Z. Liang, M.M. Li, B. Sun, L. Qin, S.P. Yang, W.H. Chen, J.X. Chen, A Zinc(II)-based two-dimensional MOF for sensitive and selective sensing of HIV-1 ds-DNA sequences, Anal. Chim. Acta. 922 (2016) 55-63.
H.Q. Zhao, S.P. Yang, N.N. Ding, L. Qin, G.H. Qiu, J.X. Chen, W.H. Zhang, W.H. Chen, T.S. Andy Hor, A zwitterionic 1D/2D polymer co-crystal and its polymorphic sub-components: a highly selective sensing platform for HIV ds-DNA sequences, Dalton Trans. 45 (2016) 5092-5100.
C. Wang, X. Liu, N. Keser Demir, J.P. Chen, K. Li, Applications of water stable metal-organic frameworks, Chem. Soc. Rev. 45 (2016) 5107-5134.
M. Chen, X.Y. Tang, S.P. Yang, H.H. Li, H.Q. Zhao, Z.H. Jiang, J.X. Chen, W.H. Chen, Five water-soluble zwitterionic copper(II)-carboxylate polymers: role of dipyridyl coligands in enhancing the DNA-binding, cleaving and anticancer activities, Dalton Trans. 44 (2015) 13369-13377.
W. Morris, W.E. Briley, E. Auyeung, M.D. Cabezas, C.A. Mirkin, Nucleic acid-metal organic framework (MOF) nanoparticle conjugates, J. Am. Chem. Soc. 136 (2014) 7261-7264.
L.F. Chen, H.Y. Zheng, X. Zhu, Z.Y. Lin, L.H. Guo, B. Qiu, G.N. Chen, Z.N. Chen, Metal-organic frameworks-based biosensor for sequence-specific recognition of double-stranded DNA, Analyst 138 (2013) 3490-3493.

(Continued)

Primary Examiner — Jezia Riley
(74) Attorney, Agent, or Firm — Renner Kenner Greive Bobak Taylor & Weber

(57) ABSTRACT

A method of preparing a crystalline copper-based coordination polymer comprises preparing a mixture of copper ions and a first quaternized carboxylate pyridyl ligand; adding a second polypyridyl ligand; and forming crystals of a copper-based coordination polymer therefrom. The crystalline copper-based coordination polymer is suitable for providing a sensing platform for detecting the presence of one or more target nucleic acid sequences such as viral RNA, in particular Dengue virus and/or Zika virus RNA with high selectivity and high specificity. A method of detecting at least a first target nucleic acid sequence, in particular from a viral RNA, in particular it is Flavivirus RNA, in a sample is also provided. Further provided is a kit including the crystalline copper-based coordination polymer and an oligonucleotide probe.

17 Claims, 10 Drawing Sheets
(2 of 10 Drawing Sheet(s) Filed in Color)
Specification includes a Sequence Listing.

(56) References Cited

PUBLICATIONS

X.F. Wei L.Y. Zheng, F. Luo, Z.Y. Lin, L.H. Guo, B. Qiu, G.N. Chen, Fluorescence biosensor for the H5N1 antibody based on a metal—organic framework platform, J. Mater. Chem. B 1 (2013) 1812-1817.

J.F. Guo, C.M. Li, X.L. Hu, C.Z. Huang, Y.F. Li, Metal-organic framework MIL-101 enhanced fluorescence anisotropy for sensitive detection of DNA, Rsc Advances 4 (2014) 9379-9382.

G.Y. Wang C. Song, D.M. Kong, W.J. Ruan, Z. Chang, Y. Li, Two luminescent metal—organic frameworks for the sensing of nitroaromatic explosives and DNA strands, J. Mater. Chem. A 2 (2014) 2213-2220.

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Synthesized

<400> SEQUENCE: 1
agaacctgtt gattcaacag cacca                                          25

<210> SEQ ID NO 2
<211> LENGTH: 25
<212> TYPE: RNA
<213> ORGANISM: Artificial Sequence
<220> FEATURE:
<223> OTHER INFORMATION: Synthesized

<400> SEQUENCE: 2
uggugcuguu gaaucaacag guucu                                          25

<210> SEQ ID NO 3
<211> LENGTH: 22
<212> TYPE: DNA
<213> ORGANISM: Artificial Sequence
<220> FEATURE:
<223> OTHER INFORMATION: Synthesized

<400> SEQUENCE: 3
gtctttccca cgtcaatatg ct                                          22

<210> SEQ ID NO 4
<211> LENGTH: 22
<212> TYPE: RNA
<213> ORGANISM: Artificial Sequence
<220> FEATURE:
<223> OTHER INFORMATION: Synthesized

<400> SEQUENCE: 4
agcauauuga cguggaaag ac                                           22

<210> SEQ ID NO 5
<211> LENGTH: 25
<212> TYPE: RNA
<213> ORGANISM: Artificial Sequence
<220> FEATURE:
<223> OTHER INFORMATION: Synthesized

<400> SEQUENCE: 5
uggugcuguu gagucaacag guucu                                       25

<210> SEQ ID NO 6
<211> LENGTH: 22
<212> TYPE: RNA
<213> ORGANISM: Artificial Sequence
<220> FEATURE:
<223> OTHER INFORMATION: Synthesized

<400> SEQUENCE: 6
agcauauuga caugggaaag ac                                          22

<210> SEQ ID NO 7
<211> LENGTH: 25
<212> TYPE: RNA
<213> ORGANISM: Artificial Sequence
<220> FEATURE:
<223> OTHER INFORMATION: Synthesized

<400> SEQUENCE: 7
ccugcugucu ccucagcauc auucc                                       25

<210> SEQ ID NO 8
<211> LENGTH: 25
<212> TYPE: RNA
<213> ORGANISM: Artificial Sequence
<220> FEATURE:
<223> OTHER INFORMATION: Synthesized

<400> SEQUENCE: 8 cgguguggg aaauccaugg uuucu                                        25

<210> SEQ ID NO 9
<211> LENGTH: 25
<212> TYPE: RNA
<213> ORGANISM: Artificial Sequence
<220> FEATURE:
<223> OTHER INFORMATION: Synthesized

<400> SEQUENCE: 9
uguagcuggu ggugaggaag aacac                                       25

```
<210> SEQ ID NO 10
<211> LENGTH: 25
<212> TYPE: RNA
<213> ORGANISM: Artificial Sequence
<220> FEATURE:
<223> OTHER INFORMATION: Synthesized

<400> SEQUENCE: 10
uuuggaugaa aaacacaaaa ccacu                                    25
```

CRYSTALLINE COPPER-BASED COORDINATION POLYMERS AND THEIR USE

SEQUENCE LISTING

The Sequence Listing file entitled "sequencelisting" having a size of 2,095 bytes and a creation date of 22 May 2017 that was filed with the patent application is incorporated herein by reference in its entirety.

TECHNICAL FIELD

The present invention relates to a method of preparing a crystalline copper-based coordination polymer comprising and especially preferably essentially but not exclusively comprising and in particular essentially consisting of copper-based coordination entities extending in three (3D) dimensions and the crystalline copper-based coordination polymer obtained or obtainable by said method. Still further, the present invention provides a method of detecting at least a first target nucleic acid sequence in a sample. The target nucleic acid sequence is in particular from a viral RNA, in particular it is Flavivirus RNA. Especially preferably but not exclusively, the method is for detecting a first and a second target nucleic acid sequence in the sample, which first target nucleic acid is Dengue virus RNA and which second nucleic acid sequence is Zika virus RNA. Further provided is a kit, which comprises the crystalline copper-based coordination polymer and an oligonucleotide probe and its use.

BACKGROUND OF THE INVENTION

Flavivirus, including the West Nile virus, Dengue virus, Japanese encephalitis virus, Yellow fever virus, Zika virus and several other viruses, are single-stranded RNA virus which causes encephalitis. Among these viruses, Dengue virus (DENV) and Zika virus (ZIKV) are two of the arthropod-borne diseases that are seriously affecting many tropical and subtropical countries. DENV and ZIKV infections have similar geographical distribution and seasonal correlation because they share the same vectors of Aedes mosquitoes for transmission. Clinical manifestations of DENV infections are often indistinguishable from ZIKV infections, making clinical diagnosis difficult. Since DENV and ZIKV infection diseases pose a large threat to human's health for its high morbidity and mortality rate and there is no effective drug or vaccine up to date, early diagnosis of virus is essential for the early discovery and isolation of the patients to control the spread of said diseases.

Currently, the diagnoses of DENV and ZIKV are based on virus isolation cultures, ELISA, genomic RNA detection using PCR and fluorescent biosensor. Among these methods, fluorescent biosensing technology has received great interest in the detection of virus nucleic acids due to its merits of high sensitivity and rapid response time. Numerous materials such as carbon nanotubes (CNTs), carbon and Au nanoparticles (CNPs and AuNPs), graphene and graphene oxides (GO), $MoS_2$ and $WS_2$, as well as metal-organic frameworks (MOFs) have been employed as quenching platforms for fluorophore-labeled nucleic acid to eliminate the high background fluorescence for the determination of target nucleic acids with enhanced sensitivity (Kumar, P. et al., Trends Analyt. Chem. 73 (2015) 39-53, Zhu, X. et al, Chem. Commun. 49 (2013) 1276-1278, Zhang, H. T. et al., Chem. Commun. 50 (2014) 12069-12072). Such development is still at an infant stage and provided MOFs often suffer from a poor water stability and/or poor water stability significantly limiting their diagnostic use as a sensing platform. Further, those materials were mainly applied for the single detection of target nucleic acids. Simultaneous and synchronous detection for multiplexed nucleic acids is rarely reported (Ye, T. et al., Analyst 139 (2014) 1721-1725). Simultaneous and synchronous fluorescence analysis for multiple nucleic acids can not only shorten the analytical time, but also improve the detection sensitivity by avoiding the interference of Raleigh light scattering signal to the fluorescence signal of the fluorophore (Xiang, D. S. et al., Science China 56 (2013) 380-386). On the other hand, simultaneous and synchronous detection is important in clinical pre-diagnosis because some indistinguishable diseases, such as DENV and ZIKV, are associated with different nucleic acids and sequences, respectively.

Accordingly, there is a strong need for improved compounds which are easily obtainable in an economic way with sufficient water stability, water solubility and sufficient DNA or RNA binding ability which are suitable to form sensing platforms for target nucleic acid sequences such as in the diagnosis of viral infectious diseases, in particular for the simultaneous and synchronous detection of viral infectious diseases.

SUMMARY OF THE INVENTION

The first aspect of the present invention relates to a method of preparing a crystalline copper-based coordination polymer. Said method of the present invention comprises steps of:

(i) preparing a mixture comprising copper ions and a first pyridyl ligand;

(ii) adding a second pyridyl ligand;

(iii) subjecting the mixture of step (ii) to conditions under which crystals of the copper-based coordination polymer are formed;

(iv) separating the crystals of the copper-based coordination polymer from the mixture.

The copper in the crystalline copper-based coordination polymer is in particular of the oxidation state +2.

The first pyridyl ligand is a quaternized carboxylate pyridyl ligand and has a structure of Formula (I):

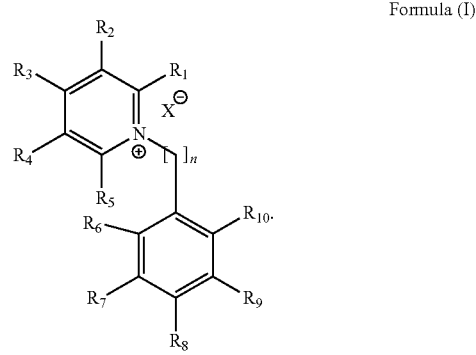

Formula (I)

X is a halogen, in particular Br, i.e. X is most preferably Br. One or more of $R_1$ to $R_5$, in particular on of $R_1$ to $R_5$, and two of $R_6$ to $R_{10}$ are a group of Formula (II):

Formula (II)

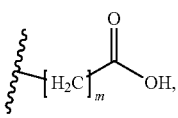

with m being an integer selected from 0, 1 or 2 and the other of $R_1$ to $R_{10}$ being hydrogen. m is in particular 0. n is an integer and selected from 0, 1 or 2. n is in particular 1.

The first pyridyl ligand in particular has a structure of Formula (III):

Formula (III)

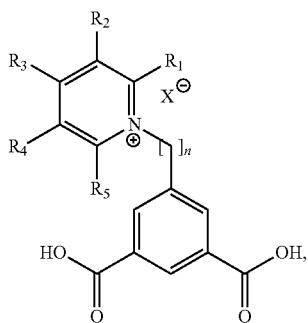

such as of Formula (IV):

Formula (IV)

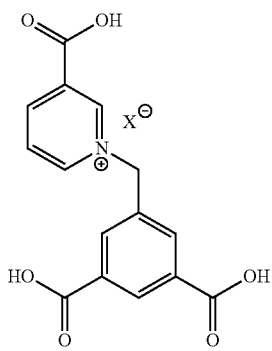

with X being a halogen and in particular Br.

The second pyridyl ligand is a polypyridyl ligand and in particular has a structure of Formula (V):

Formula (V)

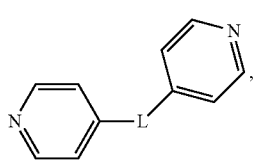

with L being a linking group selected from $-(CH_2)_{n'}-$, $-(CH=CH)_{n'}-$ or $-(N=N)_{n'}-$ with n' being an integer and selected from 0, 1, 2 or 3, such as of Formula (VI):

Formula (VI)

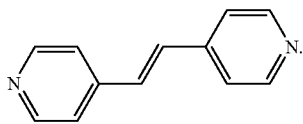

The present invention further provides a crystalline copper-based coordination polymer obtained or obtainable by the method described above. The crystalline copper-based coordination polymer in particular comprises and more preferably essentially consists of crystals with a monoclinic space group and is in particular a 3D coordination polymer.

The present invention in a third aspect provides a method of detecting at least a first target nucleic acid sequence in a sample. The sample is from a subject such as a mammal, preferably a human and can comprise, for example, blood.

The method of the present invention of detecting at least a first target nucleic acid sequence in a sample comprises steps of:

(i) preparing a mixture of a crystalline copper-based coordination polymer obtained or obtainable with the preparation method described above and at least a first oligonucleotide probe having a nucleic acid sequence at least partially complementary to said first target nucleic acid sequence and being labeled with a fluorescent;

(ii) incubating the mixture with the sample;

(iii) measuring the fluorescence after step (ii);

(iv) determining the presence and/or amount of the at least one target nucleic acid sequence in the sample based on the fluorescence determined in step (iii).

In particular, the method is for detecting a first and a second target nucleic acid sequence in the sample, which first target nucleic acid comprises or consists of SEQ. ID. NO: 2 and which second nucleic acid sequence comprises or consists of SEQ. ID. NO:4, wherein in step (i) a first and a second oligonucleotide probe is used, the first being a FAM-labeled SEQ. ID. NO: 1 and the second being a ROX-labeled SEQ. ID. NO: 3.

Still further, a kit is provided with the present invention comprising:

(i) a crystalline copper-based coordination polymer obtained or obtainable with the preparation method described above;

(ii) at least a first oligonucleotide probe having a nucleic acid sequence complementary to a first target nucleic acid sequence and being labeled with a fluorescent, in particular a FAM-labeled oligonucleotide probe of SEQ. ID. NO:1 or a ROX-labeled oligonucleotide probe of SEQ. ID. NO:3, in particular a FAM-labeled oligonucleotide probe of SEQ. ID. NO:1 and a ROX-labeled oligonucleotide probe of SEQ. ID. NO:3 are present in the kit.

In a further aspect, the present invention refers to the use of the crystalline copper-based coordination polymer obtained or obtainable by the preparation method as described above or the kit in the diagnosis of viral infectious diseases, preferably of Flavivirus, in particular Dengue virus and/or Zika virus. More specifically, the present invention refers to the use of the crystalline copper-based coordination polymer or the kit for detecting the presence and/or the amount of at least a first target nucleic acid in a sample from a subject such as a human, in particular Dengue virus RNA comprising or consisting of SEQ. ID. NO:2 and/or Zika virus RNA comprising or consisting of SEQ. ID. NO:4.

The method of the present invention allows for preparing highly advantageous water stable and water soluble crystalline copper-based coordination polymers. The inventors in particular found that [Cu(Dcbcp)(bpe)]$_n$ also referred to as compound 1 herein with high water-solubility and stability herein prepared from and comprising the zwitterionic carboxylate ligand N-(3,5-dicarboxylbenzyl)-(3-carboxyl) pyridinium bromide (H$_3$DcbcpBr) and the bridging bipyridine ancillary ligand 1,2-bis(4-pyridyl)ethylene (bpe) can form electrostatic, π stacking and/or hydrogen bonding interactions with two different fluorophore-labeled DNA probes to form two sensing systems also referred to as P-DNAs@1. Compound 1 possesses a three-dimensional (3D) open framework with large pores which are decorated by π-electron-rich benzene rings, uncoordinated carboxylates, positively charged pyridinium and Cu(II) centers. Such structural feature endows compound's 1 high affinity toward carboxyfluorescein (FAM) or 5(6)-carboxyrhodamine, triethylammonium salt (ROX)-tagged single stranded probe DNA (P-DNA), thus quenching the tag fluorescence.

These two systems proved to be highly effective fluorescent sensing platforms even allowing for a simultaneous detection of Dengue virus (DENV) and Zika virus (ZIKV) RNA sequences by single and synchronous fluorescence analysis with high selectivity and sensitivity. The inventors could not observe any cross reaction between the two DNA probes during synchronous fluorescence detection process. This type of highly promising sensing system might, thus, be used in the early diagnosis of Flavivirus infectious diseases as well as other virus associated infectious diseases which have similar clinical manifestations and geographical distributions. In the single detection, the detection time for DENV and ZIKV RNA sequences proved to be as low as 36 min and 2 min with detection limits of 332 and 192 pM, respectively. With the same detection time as single detection, synchronous fluorescence detection proved to give detection limits of 184 and 121 pM, respectively. Both assays are highly specific and not interfered by other mismatched RNA sequences, even down to single-base mismatched single strain RNA sequences. Comparing these two methods, synchronous fluorescence analysis improves the detection efficiency by saving the time and increasing the detection limits.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows the fluorescence spectrum of the P-DNA-1@1 system incubated with T$_1$ of varying concentrations. FIG. 4B shows the fluorescence spectrum of the P-DNA-2@1 system incubated with T$_2$ of varying concentrations.

FIG. 4C shows the fluorescence spectrum of the P-DNA-1@1 system in the presence of T$_1$ at varying incubation time. FIG. 4D shows the fluorescence spectrum of the P-DNA-2@1 system in the presence of T$_2$ at varying incubation time.

FIGS. 7A, 7B, and 7C show fluorescence spectra of P-DNAs@1 (50 nM/40 μM) and P-DNAs@1 with T$_1$ (60 nM), T$_2$ (60 nM), T$_1$ and T$_2$ (60 nM/60 nM), wherein FIG. 7A shows fluorescence spectra of P-DNAs@1 and P-DNAs@1 with T$_1$, FIG. 7B shows fluorescence spectra of P-DNAs@1 and P-DNAs@1 with T$_2$, and FIG. 7C shows fluorescence spectra of P-DNAs@1 and P-DNAs@1 with T$_1$ and T$_2$.

DETAILED DESCRIPTION OF THE INVENTION

Figure 1A:
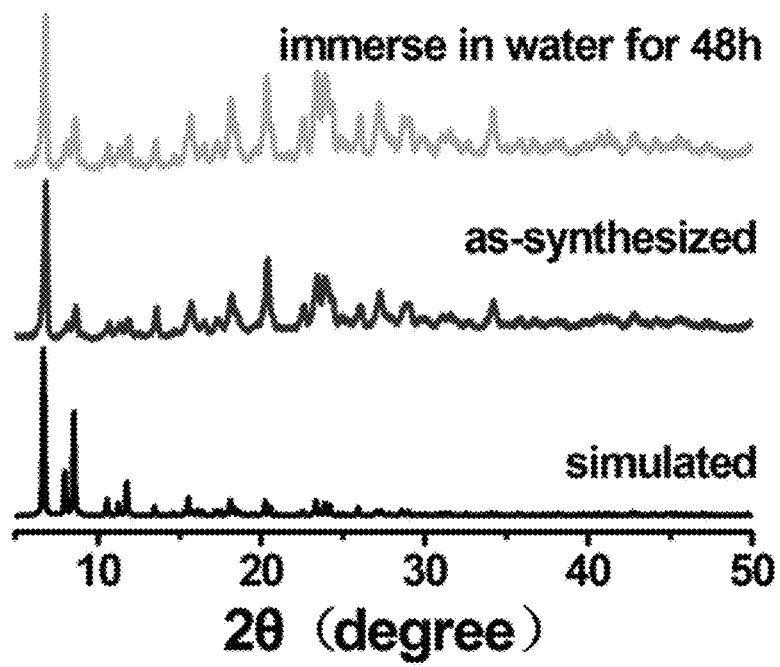
FIG. 1A shows PXRD patterns of the crystalline copper-based coordination polymer [Cu(Dcbcp)(bpe)]$_n$ (compound 1) showing agreement among the simulated, synthesized and fresh powder of compound 1 immersed in H$_2$O for 48 h.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. The expression that a material "is" a certain element as used herein such as that a solvent is water or the like means that the material essentially consists of said element. As used herein, the forms "a," "an," and "the," are intended to include the singular and plural forms unless the context clearly indicates otherwise.

The present invention provides a method of preparing a crystalline copper-based coordination polymer.

Said term "copper-based coordination polymer" refers to a compound comprising and in particular essentially consisting of copper-based coordination entities. A "coordination entity" possesses a copper ion bound to other atoms or groups of components referenced as ligands. The term "ligands" refers to the components with groups or atoms bound to the copper ion, thereby the copper ion usually occupies a central position in said coordination entity. Preferably, the crystalline copper-based coordination polymer comprises and in particular essentially consists of repeating coordination entities extending in three dimensions (3D), i.e. is a 3D coordination polymer.

The expression "essentially consisting of" in relation to the crystalline copper-based coordination polymer does not exclude that further ions or water molecules from the preparation process are still present in the compound.

The copper-based coordination polymer prepared according to the method of the present invention is crystalline, which shall mean that the atoms or molecules are substantially organized in a structure known as a crystal. Said term is generally used in the art for any structure of ions, molecules, or atoms that are held together in an ordered arrangement. A crystalline structure is one of two types of structural ordering of atoms, ions or molecules the other being the amorphous structure which is irregular and lacks an orderly arrangement of structural units. Whether a compound is crystalline and the respective crystal system can, for example, be confirmed by means of X-ray diffraction. Preferably, the copper-based coordination polymer comprises and in particular essentially consists of crystals possessing a monoclinic space group.

The method of the present invention comprises steps of:
(i) preparing a mixture comprising copper ions and a first pyridyl ligand;
(ii) adding a second pyridyl ligand;
(iii) subjecting the mixture of step (ii) to conditions under which crystals of the copper-based coordination polymer are formed;
(iv) separating the crystals of the copper-based coordination polymer from the mixture.

The copper in the crystalline copper-based coordination polymer is preferably of the oxidation state +2.

The first pyridyl ligand is a quaternized carboxylate pyridyl ligand. The term "pyridyl ligand" as used herein generally refers to a ligand comprising at least one optionally substituted pyridine ring.

The first pyridyl ligand is a pyridyl ligand which has carboxylic acid moieties referred to as "carboxylate ligand", which means herein free carboxylic acid functions. The term "quaternized" as used herein means that the pyridyl ligand has at least one quaternary ammonium salt group, i.e. at least one positively charged moiety comprising a nitrogen atom, which nitrogen atom binds to carbon atoms via four covalent bonds. In particular, the pyridyl ligand is a zwitterionic quaternized carboxylate pyridyl ligand, i.e. is a molecule with both positive and negative charges.

The first pyridyl ligand has a structure of Formula (I):

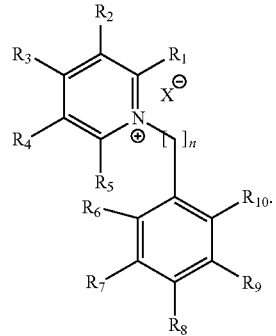

Formula (I)

X is a halogen, i.e. $X^-$ is a halogen ion, in particular selected from Cl, Br or I and most preferably Br, i.e. $X^-$ is most preferably Br. One or more of $R_1$ to $R_5$, in particular one of $R_1$ to $R_5$, and two of $R_6$ to $R_{10}$ are a group of Formula (II):

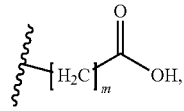

Formula (II)

with m being an integer selected from 0, 1 or 2 and the other of $R_1$ to $R_{10}$ being hydrogen. m is most preferably 0, i.e. the carboxyl groups are directly attached to carbon atoms in the benzene and/or pyridine ring. n is an integer and selected from 0, 1 or 2. n is more preferably 1.

Further preferred, $R^7$ and $R^9$ are a group of formula (II). In such embodiments of the present invention, the first pyridyl ligand more preferably has a structure of Formula (III):

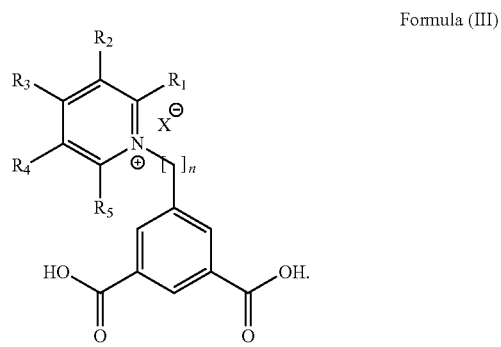

Formula (III)

Still more preferred, $R_2$, $R_7$ and $R_9$ are a group of Formula (II). In such embodiments of the present invention, the first pyridyl ligand more preferably has a structure of Formula (IV):

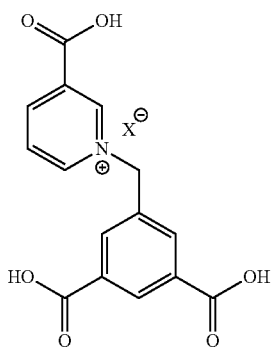

Formula (IV)

with X being a halogen and in particular Br.

In most preferred embodiments of the present invention, the first pyridyl ligand has a structure of Formula (IV).

The feature that the mixture of step (i) comprises the first pyridyl ligand as used herein is to be understood to cover any protonated or deprotonated form of said pyridyl ligand due to the presence of further components in the mixture added, for example, for dissolving it.

The second pyridyl ligand is a polypyridyl ligand, which means a ligand containing two or more optionally substituted pyridine ring which are covalently linked to each other and may optionally form a larger ring system. Preferred second pyridyl ligands have a structure of Formula (V):

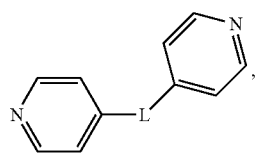

Formula (V)

with L being a linking group selected from —(CH$_2$)$_{n'}$—, —(CH=CH)$_{n'}$— or —(N=N)$_{n'}$— with n' being an integer and selected from 0, 1, 2 or 3, in particular from 1 or 2.

For example, the second pyridyl ligand could have a structure selected from:

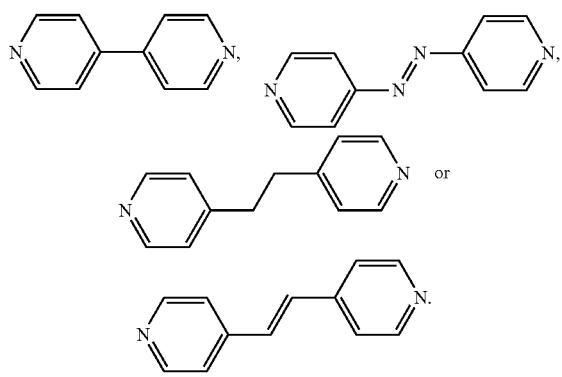

Most preferably, the second pyridyl ligand has a structure of Formula (VI):

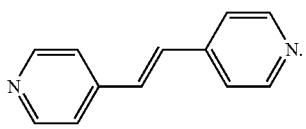

Formula (VI)

In particular embodiments of the present invention, the first pyridyl ligand has a structure of Formula (IV):

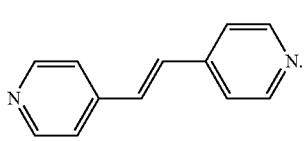

Formula (IV)

with X being as defined as above, in particular being Br and the second pyridyl ligand has a structure of Formula (VI):

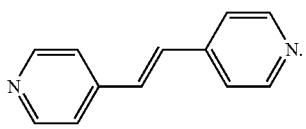

Formula (VI)

Step (i) preferably comprises steps of:
a) preparing a first pre-mixture comprising mixing the first pyridyl ligand and a solvent;
b) preparing a second pre-mixture comprising mixing a copper salt and a solvent;
c) adding the second pre-mixture to the first pre-mixture;
d) stirring the mixture at a temperature of about 20° C. to about 30° C. for at least about 10 min.

The first pyridyl ligand can be in form of a powder.

The solvents in step a) and step b) preferably comprise water. The solvents in step a) and step b) most preferably essentially consist of water. I.e., in especially preferred embodiments, both solvents in step a) and step b) essentially consist of water.

Step a) preferably further comprises a step of adjusting the pH to a pH of between about 6.5 and about 7.5, more preferably to a pH of about 7. The pH is preferably adjusted by adding a base. The base is preferably an alkali hydroxide. Alkali hydroxides are a class of chemical compounds which are composed of an alkali metal cation, i.e. one of lithium (Li), sodium (Na), potassium (K), rubidium (Rb), caesium (Cs), and the hydroxide anion (HO—). In particular, the alkali metal cation is K or Na. More preferably, the base is NaOH such as 0.1M NaOH, i.e. sodium hydroxide. In such embodiments, the first pre-mixture comprises the solvent of step a) and NaOH.

The copper salt is preferably a salt of copper of the oxidation state +2, in particular it is a hydrate of CuSO$_4$, in particular the pentahydrate. Thus, the copper salt is most preferably CuSO$_4$×5 H$_2$O.

The first pre-mixture can be prepared by suspending the first pyridyl ligand in the solvent.

The first pyridyl ligand in step a) is preferably used in a molar ratio compared to the copper salt in step b) of about 0.8:1 to about 1.4:1 and more preferably of about 1:1.

The stirring in step d) is preferably carried out for about 30 min. The temperature is more preferably about 25±2° C.

The mixture prepared in step (i) is preferably a solution, i.e. a homogeneous mixture comprising the copper ions and the first pyridyl ligand in the solvents from step a) and b) and optionally the base.

Step (ii) of adding a second pyridyl ligand is preferably carried out by adding a mixture such as a solution of the second pyridyl ligand in a solvent. The solvent preferably comprises and in particular essentially consists of an amide, in particular dimethylformamide (DMF). The second pyridyl ligand is preferably used in a molar ratio to the copper salt of about 0.8:1 to about 1.4:1 and more preferably of about 1:1. In particular embodiments of the present invention, first pyridyl ligand, copper salt and second pyridyl ligand are used in a molar ratio of about 1:1:1.

Step (iii) of subjecting the mixture of step (ii) to conditions under which crystals of the copper-based coordination polymer are formed in particular includes steps of:
a) stirring the mixture at a temperature of about 20° C. to about 30° C., in particular of about 25±2° C.;
b) filtering the mixture for obtaining a filtrate and a residue;
c) heating the filtrate to a temperature of at least about 80° C., further preferred to about 100° C. for at least about 30 min and in particular for about 60 min;
d) allowing the filtrate to stand at a temperature of at least about 80° C. and in particular at about 100° C. for at least about 48 h and in particular for about 72 hours;
e) allowing the mixture after step d) to cool down to a temperature of about 25° C. to about 35° C., in particular to about 30° C. for at least about 24 h, in particular for about 48 h.

The method of the present invention further comprises a step (iv) of separating the crystals of the copper-based coordination polymer. Said step (iv) preferably comprises steps of:
a) separating the crystals from the mixture;
b) purifying the crystals;
c) drying the crystals, preferably by drying the crystals in vacuo.

Preferably, purifying the crystals in step b) comprises and in particular is carried out by means of washing the crystals with a washing solvent. The washing solvent preferably comprises a dialkyl ether, in particular diethyl ether.

The first pyridyl ligand is most preferably of Formula (IV):

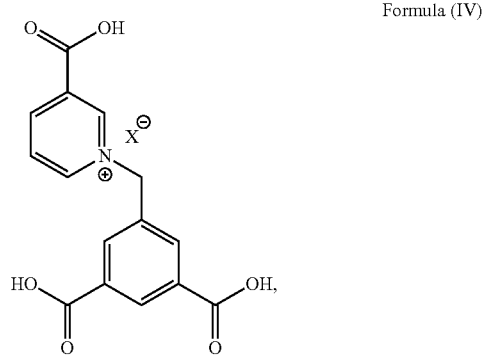

Formula (IV)

with X being Br. In such embodiments, the method of the present invention may further comprise preparing the first pyridyl ligand before step (I) comprising steps of:
a) providing a mixture of a compound of Formula (VII) and a compound of Formula (VIII) in a solvent:

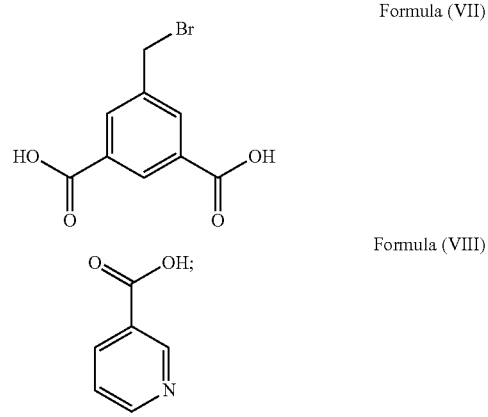

Formula (VII)

Formula (VIII)

b) stirring the mixture of step a) for at least about 4 h, in particular for about 8 h at a temperature of about 20° C. to about 30° C., in particular of about 25±2° C. for forming a precipitate;
c) separating the precipitate from the mixture of step b) in particular by filtration and optionally purifying the precipitate such as by washing with a washing solvent and drying the precipitate preferably in vacuo. The washing solvent is preferably selected from an amide, a ketone or mixtures thereof, in particular from dimethylformamide, acetone or mixtures thereof and most preferably it is a mixture of dimethylformamide and acetone.

The solvent in step a) is preferably an amide, more preferably dimethylformamide. In particular, the compound of Formula (VII) is first mixed, in particular dissolved in the solvent and added to a mixture, in particular a solution, of the compound of Formula (Viii) in the solvent.

The present invention in particular encompasses the following preferred embodiment of the method of the present invention:

The first pyridyl ligand used in step (i) is of Formula (IV):

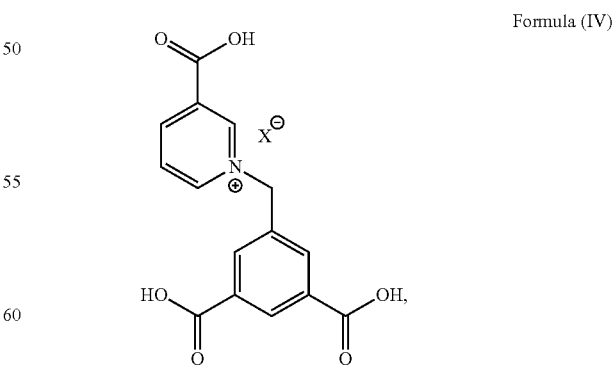

Formula (IV)

with X being Br, i.e. N-(3,5-dicarboxylbenzyl)-(3-carboxyl) pyridinium bromide (H$_3$DcbcpBr), the copper salt is CuSO$_4$×5 H$_2$O and the second pyridyl ligand is of Formula (VI):

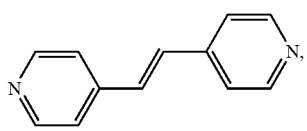

Formula (VI)

i.e. is 1,2-bis(4-pyridyl)ethylene (bpe), wherein the first pyridyl ligand, the copper salt and the second pyridyl ligand are preferably used in a molar ratio of about 1:1:1. In such embodiment, the crystalline copper-based coordination polymer preferably comprises and in particular essentially consists of repeating coordination entities extending in three dimensions (3D), i.e. is a 3D coordination polymer, comprising and in particular essentially consisting of asymmetric units with the formula [Cu(Dcbcp)(bpe)], i.e. which crystalline copper-based coordination polymer can in embodiments be described as [Cu(Dcbcp)(bpe)]$_n$ crystalizing in a monoclinic space group (also referenced as compound 1). As used herein, "asymmetric unit" means the minimal set of atomic coordinates that can be used to generate the entire repetition in a crystal.

The present invention further provides a crystalline copper-based coordination polymer obtained or obtainable by the method described above. In one embodiment, the present invention provides a copper-based coordination polymer obtained by the method described above. In another embodiment, the present invention provides a crystalline copper-based coordination polymer obtainable by the method described above. The crystalline copper-based coordination polymer preferably comprises and more preferably essentially consists of crystals with a monoclinic space group.

The crystalline copper-based coordination polymer in preferred embodiments of the present invention comprises repeating coordination entities extending in three dimensions, i.e. more preferably is a 3D coordination polymer.

The crystalline copper-based coordination polymer is in preferred embodiments obtained or obtainable by the method described above in which the first pyridyl ligand in step (i) has a structure of Formula (IV):

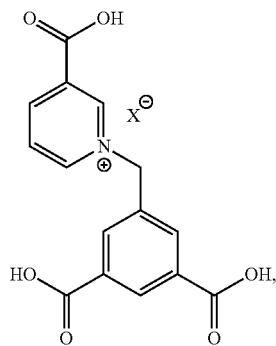

Formula (IV)

with X being Br and the second pyridyl ligand is of Formula (VI):

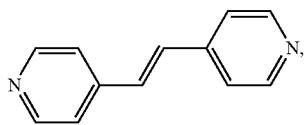

Formula (VI)

which crystalline copper-based coordination polymer can be described by the formula [Cu(Dcbcp)(bpe)]$_n$, i.e. is compound 1.

The crystalline copper-based coordination polymer is in particular water stable which can be confirmed with powder X-ray diffraction measurements of powder of the copper-based coordination polymer immersed in water for about 48 h compared to the as-synthesized and simulated pattern. The crystalline copper-based coordination polymer is in particular stable up to a temperature of about 200° C. which can be confirmed by means of thermogravimetric analyses.

The present invention in a third aspect provides a method of detecting a target nucleic acid sequence in a sample. The sample is from a subject such as a mammal, preferably a human and can comprise, for example, blood.

The method of the present invention of detecting at least a first target nucleic acid sequence in a sample comprises steps of:

(i) preparing a mixture of a crystalline copper-based coordination polymer obtained or obtainable with the preparation method described above and at least a first oligonucleotide probe having a nucleic acid sequence at least partially complementary to said first target nucleic acid sequence and being labeled with a fluorescent;

(ii) incubating the mixture with the sample;

(iii) measuring the fluorescence after step (ii);

(iv) determining the presence and/or amount of the at least one target nucleic acid sequence in the sample based on the fluorescence determined in step (iii).

The crystalline copper-based coordination polymer used in step (i) is preferably obtained or obtainable by the method described above in which the first pyridyl ligand in step (i) has a structure of Formula (IV):

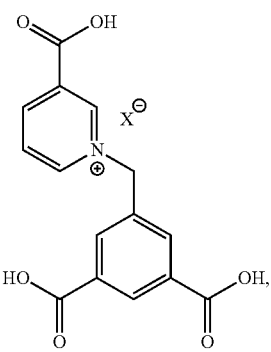

Formula (IV)

with X being Br and the second pyridyl ligand is of Formula (VI):

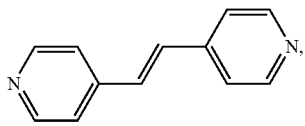

Formula (VI)

which crystalline copper-based coordination polymer can be described by the formula [Cu(Dcbcp)(bpe)]$_n$, i.e. is more preferably compound 1.

Said compound proved to allow for an exceptional interaction with oligonucleotide probes of SEQ. ID. NO: 1 and SEQ. ID. NO: 3. The inventors further found that such crystalline copper-based coordination polymers provide an exceptional quenching efficiency and fluorescence recovery efficiency with high specificity and selectivity and with detection limits in the picomolar range when using Dengue and Zika virus RNA sequences. In particular, said compound proved to be highly advantageous for a synchronous detection of Dengue and Zika virus RNA sequences.

In embodiments of the method of the present invention for detecting at least a first target nucleic acid sequence in a sample, the method ifs for detecting a first and a second target nucleic acid sequence in the sample, wherein in step (i) a first and a second oligonucleotide probe is used, the first having a nucleic acid sequence at least partially complementary to the first target nucleic acid sequence and being labeled with a fluorescent and the second having a nucleic acid sequence at least partially complementary to the second target nucleic acid sequence and being labeled with a fluorescent.

The target nucleic acid sequence is preferably RNA, in particular viral RNA such as from Flavivirus, in particular from Dengue virus comprising or in particular consisting of a sequence having SEQ. ID. NO:2 and/or from Zika virus comprising or in particular consisting of a sequence having SEQ. ID. NO:4. Said part of the Flavivirus RNA includes nucleotide sequences very specific for the respective type of Flavivirus.

The term "oligonucleotide probe" as known in the art refers to a short single-stranded sequence of nucleotides that are synthesized to match a specific region of target nucleic acid sequence used as a molecular probe to detect said sequence. Said oligonucleotide probe is labeled with a fluorescent, more preferably FAM (6-carboxyfluorescein/fluorescein) or 5(6)-carboxyrhodamine/carboxy-X-rhodamine (ROX) is attached to the oligonucleotide probe. The oligonucleotide probe is preferably made up of 15 to 30 nucleotides and more preferably comprises a sequence of SEQ. ID. NO: 1 or SEQ. ID. NO:3, most preferably it is a FAM-labeled ss-DNA sequence comprising or consisting of SEQ. ID. NO:1 or a ROX-labeled ss-DNA sequence comprising or consisting of SEQ. ID. NO:3.

The incubation in step (ii) of the method of detecting a target nucleic acid sequence may be carried out for about 1 min to about 40 min.

The wavelength for determining the fluorescence in step (iii) of the method of detecting a target nucleic acid sequence depends on the fluorescent. The skilled person is able to determine the respective absorption and emission wavelength.

Step (iv) may further comprise a step of comparing the fluorescence with at least one reference value such as the fluorescence of a reference sample without the at least first target nucleic acid sequence or at least one reference sample with a predetermined amount of the at least first target nucleic acid sequence.

The inventors found that in step (i) the crystalline copper-based coordination polymer can non-covalently bind to the oligonucleotide probe and thereby quench the fluorescence of said oligonucleotide probe. The oligonucleotide probe in step (ii) can then bind to its target nucleic acid sequence in the sample leading to fluorescence regeneration.

Hence, the method and the crystalline copper-based coordination polymer can in particular be used in the diagnosis of Flavivirus such as Dengue virus and/or Zika virus.

In most preferred embodiments of the method, the method ifs for detecting a first and a second target nucleic acid sequence in the sample, which first target nucleic acid comprises and more preferable consists of SEQ. ID. NO: 2 and which second nucleic acid sequence comprises and more preferably consists of SEQ. ID. NO:4, wherein in step (i) a first and a second oligonucleotide probe is used, the first being a FAM-labeled SEQ. ID. NO: 1 and the second being a ROX-labeled SEQ. ID. NO: 3.

Still further, a kit is provided with the present invention comprising:

(i) a crystalline copper-based coordination polymer obtained or obtainable with the preparation method described above;

(ii) at least a first oligonucleotide probe having a nucleic acid sequence complementary to a first target nucleic acid sequence and being labeled with a fluorescent, in particular a FAM-labeled oligonucleotide probe of SEQ. ID. NO:1 or a ROX-labeled oligonucleotide probe of SEQ. ID. NO:3, in particular a FAM-labeled oligonucleotide probe of SEQ. ID. NO:1 and a ROX-labeled oligonucleotide probe of SEQ. ID. NO:3 are present in the kit.

The crystalline copper-based coordination polymer in the kit is preferably obtained or obtainable by the preparation method described above in which the first pyridyl ligand in step (i) of the preparation method has a structure of Formula (IV):

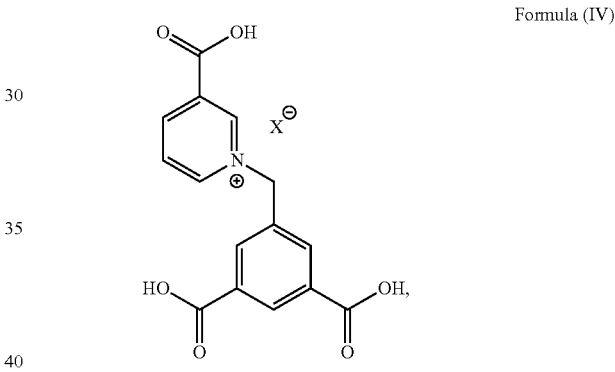

Formula (IV)

with X being Br and the second pyridyl ligand is of Formula (VI):

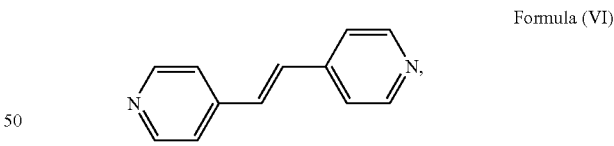

Formula (VI)

which crystalline copper-based coordination polymer can be described by the formula $[Cu(Dcbcp)(bpe)]_n$, i.e. is more preferably compound 1.

In a further aspect, the present invention refers to the use of the crystalline copper-based coordination polymer obtained or obtainable by the preparation method as described above or the kit in the diagnosis of viral infectious diseases, preferably of Flavivirus, in particular Dengue virus and/or Zika virus. More specifically, the present invention refers to the use of the crystalline copper-based coordination polymer or the kit for detecting the presence and/or the amount of at least a first target nucleic acid in a sample from a subject such as a human, in particular Dengue virus RNA comprising or consisting of SEQ. ID. NO:2 and/or Zika virus RNA comprising or consisting of SEQ. ID. NO:4.

EXAMPLES

Powder X-ray diffraction (PXRD) was performed using a Rigaku D/max-2200/PC Diffractometer (Rigaku, Japan) with radiation of Cu target ($\lambda$ Cu-K$\alpha$=1.54178 Å). $^1$H NMR spectra was recorded using a Bruker Avance AV 400 spectrometer (Bruker, Switzerland). IR spectrum was recorded on a Nicolet MagNa-IR 550 infrared spectrometer (Thermo Fisher, USA) as KBr pellets in the 400-4000 cm$^{-1}$ region. Elemental analysis (C, H and N) was carried out on a FLASH EA1112 Elemental Analyzer (Thermo Fisher, USA). Crystallographic measurement was made on a Bruker APEX II diffractometer (Bruker, Germany) with a graphite-monochromated Mo K$\alpha$ ($\lambda$=0.71073 Å) irradiation. Fluorescence spectra were measured on an LS55 spectrofluorimeter (Perkinelmer, USA).

All chemicals with reagent grade quality were obtained from commercial sources and used without further purification. All the DNA and RNA sequences were purchased from Sangon Inc. (Shanghai, China) and are given in Table 1.

All the DNA and RNA samples were prepared in 100 μM Tris-HCl buffer solution (pH 7.4, 100 mM NaCl, 5 mM MgCl$_2$) and stored at 4° C. (DNA) or −80° C. (RNA) for use.

Example 1

Synthesis of a Crystalline Copper-Based Coordination Polymer of the Present Invention
Synthesis of Ligand H$_3$DcbcpBr A solution of 5-(bromomethyl)isophthalic acid (0.518 g, 2 mmol) in DMF (10 mL) was added to 3-pyridinecarboxylic acid (0.246 g, 2 mmol) in DMF (90 mL). The clear solution was stirred for 8 h at room temperature and the resulting white precipitate was collected by filtration and washed with DMF/acetone (20 mL, v:v=1:1). Ligand of H$_3$DcbcpBr was obtained after drying under vacuum. Yield: 0.581 g (76%). $^1$H-NMR (400 MHz, D$_2$O) δ 9.34 (s, 1H), 8.96 (d, J=6 Hz, 1H), 8.89 (d, J=8 Hz, 1H), 8.36 (s, 1H), 8.12 (t, J=6.4 Hz, 1H), 8.05 (s, 2H), 5.99 (s, 2H). Anal. Calcd. For C$_{15}$H$_{12}$NO$_6$Br: C 47.14, H 3.16, N 3.67. Found: C 47.53, H

TABLE 1

| DNA and RNA sequences used in the present invention | | | |
|---|---|---|---|
| | comprises SEQ. ID. NO. | Sequence | |
| oligonucleotide probe/probe DNA of DENV (P-DNA-1) | FAM-labeled SEQ. ID. NO: 1 | 5'-FAM-AGAACCTGTTGATTCAACAGCACCA-3' | |
| Complementary target DENV RNA (T$_1$) | SEQ. ID. NO: 2 | 5'-UGGUGCUGUUGAAUCAACAGGUUCU-3' (GenBank No. KT187556.1) | |
| oligonucleotide probe/probe DNA of DENV (P-DNA-2) | ROX-labeled SEQ. ID. NO: 3 | 5'-ROX-GTCTTTCCCACGTCAATATGCT-3' | |
| Complementary target ZIKV RNA (T$_2$) | SEQ. ID. NO: 4 | 5'-AGCAUAUUGACGUGGGAAAGAC-3' (GenBank No. AY632535.2) | |
| Single-base pair mutated RNA sequence for DENV (T$_1$') | SEQ. ID. NO: 5 | 5'-UGGUGCUGUUGAGUCAACAGGUUCU-3' | |
| Single-base pair mutated RNA sequence for ZIKV (T$_2$') | SEQ. ID. NO: 6 | 5'-AGCAUAUUGACAUGGGAAAGAC-3' | |
| Non-specific RNA sequences | | | |
| T$_A$ of DENV | SEQ. ID. NO: 7 | 5'-CCUGCUGUCUCCUCAGCAUCAUUCC-3' (GenBank No. KT187556.1) | |
| T$_B$ of ZIKV | SEQ. ID. NO: 8 | 5'-CGGUGUGGGGAAAUCCAUGGUUUCU-3' (GenBank No. AY632535.2) | |
| Specific RNA sequences of closely related Flavivirus | | | |
| T$_C$ of Japanese encephalitis virus | SEQ. ID. NO: 9 | 5'-UGUAGCUGGUGGUGAGGAAGAACAC-3' (GenBank No. AY303791.1) | |
| T$_D$ of Yellow fever virus | SEQ. ID. NO: 10 | 5'-UUUGGAUGAAAAACACAAAACCACU-3' (GenBank No. AF094612.1). | |

3.20, N 3.28. IR (KBr disc, cm$^{-1}$) v 3457 (m), 3264 (s), 1624 (s), 1573 (m), 1321 (m), 1211 (s), 1160 (m), 1138 (s), 1021 (s), 864 (m), 748 (s), 665 (s), 627 (m), 573 (m), 527 (m), 436 (m).

Synthesis of [Cu(Dcbcp)(bpe)]$_n$ (compound 1)

Powder of H$_3$DcbcpBr (76.4 mg, 0.2 mmol) was suspended in H$_2$O (20 mL) and the pH adjusted to 7.0 with 0.1 M NaOH to give a clear solution. To the clear solution was added a solution of CuSO$_4$.5H$_2$O (50 mg, 0.2 mmol) in H$_2$O (20 mL). The resulting mixture was stirred for 0.5 h to give a clear light blue solution. A solution of bpe (36 mg, 0.2 mmol) in DMF (2 mL) was then added and stirred gently for a while to give a blue solution. After filtration, the filtrate was heated from 25° C. to 100° C. for 1 h and maintained at 100° C. for 72 h before smoothly cooling from 100° C. to 30° C. in 48 h. Green block-shape crystals of compound 1 were collected and washed with diethyl ether and dried under vacuum. Yield: 92 mg (84%). Anal. Calcd. for C$_{27}$H$_{19}$N$_3$OCu.H$_2$O: C 57.54, H 3.73, N 7.46. Found: C 57.42, H 3.76, N, 7.28. IR (KBr disc, cm$^{-1}$) v 3546 (s), 3038 (m), 1604 (s), 1436 (s), 1162 (m), 1067 (m), 983 (m), 816 (m), 746 (m), 718 (m), 671 (m), 559 (m), 457 (m).

Example 2

X-Ray Crystal Structure Determinations of the Obtained Crystalline Copper-Based Coordination Polymer All data were collected using the ω-2θ scan technique and corrected for Lorenz-polarization effects with the SMART suite of programs and for absorption effects with SADABS (Skořepová, E. et al., Cryst. Growth. Des. 13 (2013) 5193-5203). The structure was solved by direct method and refined on F$^2$ by full-matrix least-squares using SHELXTL-97 program (Sheldrick, G. M., SHELX-97 and SHELXL-97, Program for crystal structure refinement, University of Göttingen, Göttingen, 1997). The non-hydrogen atoms were refined with anisotropic thermal parameters. A large amount of spatially delocalized electron density in the lattice was found but acceptable refinement results could not be obtained for this electron density. The solvent contribution was then modeled using SQUEEZE in the Platon program suite (Spek, A. L., Acta Crystallogr. C Struct. Chem. 71 (2015) 9-18). The detailed crystallographic parameters of compound 1 are listed in Table 2, selected bond lengths and angles in Table 3.

Characterization of [Cu(Dcbcp)(bpe)]$_n$ (compound 1)

MOFs can be divided into one-dimensional chain (lD), two-dimensional (2D) layer and 3D structure according to their spatial arrangements. Among these structures, 3D structures endow MOF more features such as porosity and in turn larger surface area. It is well accepted that the introduction of bridging auxiliary ligands in the construction process can increase the possibility of forming MOFs with large pores through the spatial dimension extension. In this invention, an ancillary bidentate ligand bpe was introduced into the construction of Cu(II) zwitterionic carboxylate complex leading to MOFs with porous 3D structure. Fortunately, the inventors were able to obtain [Cu(Dcbcp)(bpe)]$_n$ (compound 1) showing large void space of 2043.8 Å$^3$ per cell (32.5% of the total cell volume).

Figure 1B:
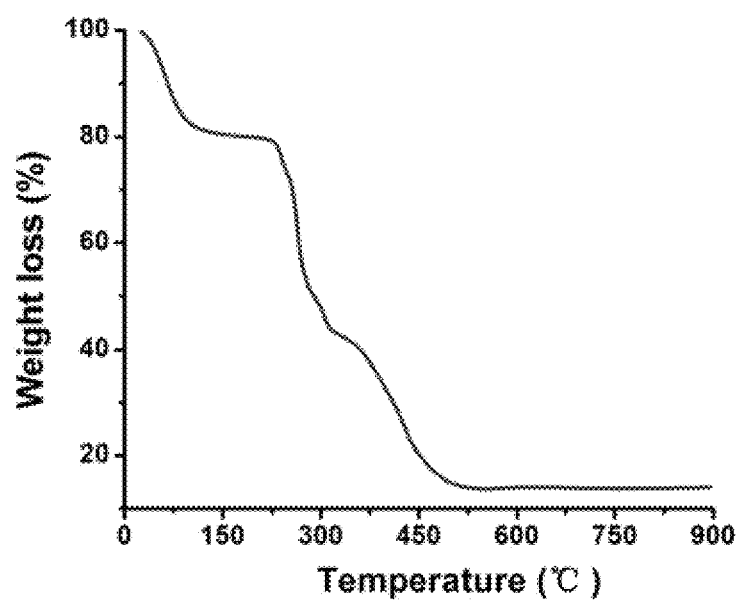
FIG. 1B shows the weight loss of compound 1 at various temperatures, i.e. from 0° C. to 900° C., in thermogravimetric analysis.

Water stability of MOFs is the key from the view of practical application for virus nucleic acid detection in biological media. Therefore the stability of compound 1 in aqueous solution was studied. It can be seen from FIG. 1A that powder X-ray diffraction (PXRD) patterns of as-synthesized compound 1 and its fresh powder immersed in H$_2$O for 48 h are in agreement with that of the simulated, indicating both of its bulky phase purity and water stability. Thermogravimetric analyses (TGA) indicated that sample of compound 1 is stable up to 200° C. (FIG. 1B). These facts suggest that compound 1 has good water and thermal stability.

Figure 2A:
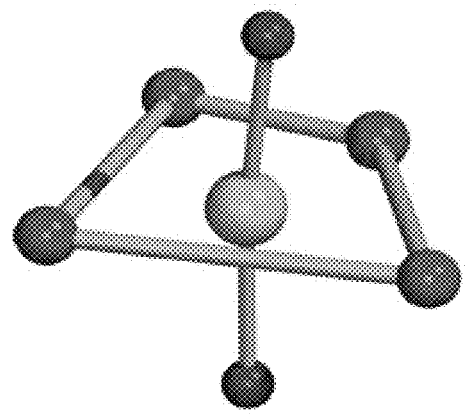
FIG. 2A illustrates the coordination mode of the Cu(II) ion.
Figure 2B:
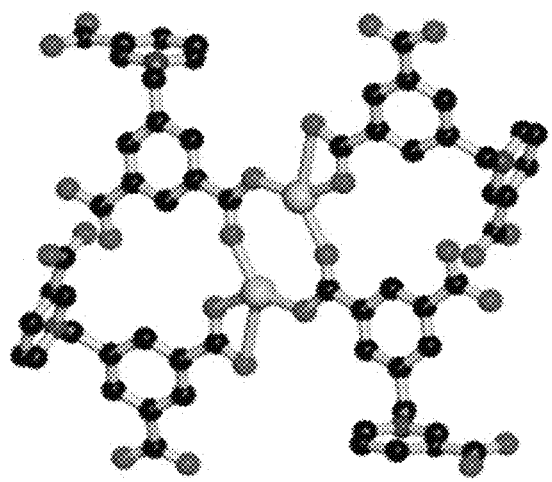
FIG. 2B illustrates the [Cu$_2$(Dcbcp)$_4$] subunit structure in compound 1.
Figure 2C:
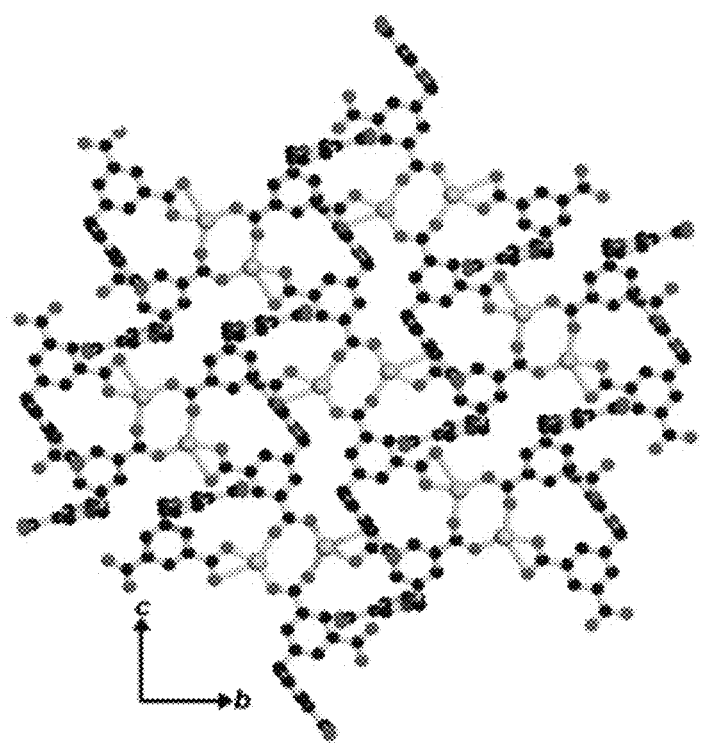
FIG. 2C shows the 2D plane sheet structure constructed by [Cu$_2$(Dcbcp)$_4$] units.
Figure 2D:
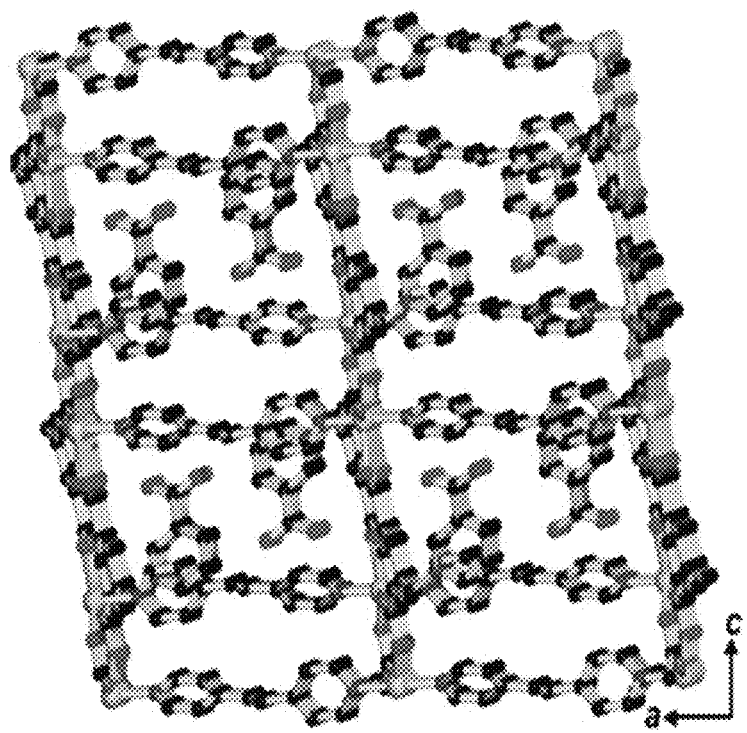
FIG. 2D shows the 3D structure of compound 1. Color codes: Cu (turquoise), O (red), N (blue), C (black).

Single-crystal X-ray analysis reveals that compound 1 crystallizes in monoclinic space group C2/c and the asymmetric unit consists of one [Cu(Dcbcp)(bpe)] molecule. As shown in FIG. 2, each Cu center is coordinated by two N atoms from two bpe molecules and four O atoms from three carboxylate groups of three Dcbcp ligands, in which two are in monodentate coordination mode and the third in chelating coordination mode, thereby forming a slightly distorted octahedron coordination geometry (FIG. 2A). Each two Cu(II) ions are linked by a couple of μ-COO groups and each Cu(II) ion further coordinated one chelating carboxylate, thereby forming a [Cu$_2$(dcbcp)$_4$] unit (FIG. 2B). Such a unit extends to six equivalents to form a 2D structure along bc plane as shown in FIG. 2C. Each Cu(II) ion is further coordinated by two bpe ligands in a direction, thereby forming a 3D structure as shown in FIG. 2D.

TABLE 2

Crystallographic data for compound 1

| Molecular formula | C$_{27}$H$_{19}$N$_3$O$_6$Cu | D$_{calc}$ (g cm$^{-3}$) | 1.152 |
|---|---|---|---|
| Crystal system | monoclinic | λ (Mo Kα) (Å) | 0.71073 |
| Formula weight | 545.00 | μ (cm$^{-1}$) | 0.733 |
| Space group | C2/c | Total reflections | 20702 |
| a (Å) | 30.9905(12) | Unique reflections | 8234 |
| b (Å) | 12.1197(6) | No. Observations | 4925 |
| c (Å) | 19.7170(7) | No. Parameters | 334 |
| α (°) | 90.00 | R$^a$ | 0.0603 |
| β (°) | 121.969(4) | wR$^b$ | 0.1475 |
| γ (°) | 90.00 | GOF$^c$ | 0.948 |
| V (Å$^3$) | 6282.4(5) | Δρ$_{max}$ (e Å$^{-3}$) | 0.708 |
| Z | 8 | Δρ$_{min}$ (e Å$^{-3}$) | −0.518 |
| T/K | 293(2) | | |

$^a$R = Σ||F$_o$| − |F$_c$|/Σ|F$_o$|.
$^b$wR = {Σw(F$_o^2$ − F$_c^2$)$^2$/Σw(F$_o^2$)$^2$}$^{1/2}$.
$^c$GOF = {Σ[w((F$_o^2$ − F$_c^2$)$^2$)/(n − p)]}$^{1/2}$, where n = number of reflections and p = total numbers of parameters refined

TABLE 3

Selected bond lengths [Å] and angles [°] for compound 1

| bond lengths [Å] | | | |
|---|---|---|---|
| Cu(1)—O(5)#1 | 1.959(2) | Cu(1)—O(1) | 2.009(2) |
| Cu(1)—N(3)#2 | 2.038(3) | Cu(1)—N(2) | 2.040(2) |
| Cu(1)—O(6)#3 | 2.203(2) | | |

TABLE 3-continued

Selected bond lengths [Å] and angles [°] for compound 1 bond angles [°]

| | | | |
|---|---|---|---|
| O(5)#1—Cu(1)—O(1) | 144.78(9) | O(5)#1—Cu(1)—N(3)#2 | 90.48(9) |
| O(1)—Cu(1)—N(3)#2 | 86.88(10) | O(5)#1—Cu(1)—N(2) | 94.94(9) |
| O(1)—Cu(1)—N(2) | 90.62(9) | N(3)#2—Cu(1)—N(2) | 173.63(11) |
| O(5)#1—Cu(1)—O(6)#3 | 123.97(8) | O(1)—Cu(1)—O(6)#3 | 91.09(9) |
| N(3)#2—Cu(1)—O(6)#3 | 88.35(10) | N(2)—Cu(1)—O(6)#3 | 85.83(10) |
| C(1)—O(1)—Cu(1) | 110.19(19) | C(8)—O(5)—Cu(1)#4 | 124.6(2) |
| C(8)—O(6)—Cu(1)#5 | 159.6(2) | C(25)—N(3)—Cu(1)#6 | 123.3(2) |
| C(26)—N(3)—Cu(1)#6 | 119.5(2) | | |

Symmetry transformations used to generate equivalent atoms: #1: x, −y, z − ½; #2: x + ½, −y + ½, z + ½; #3: −x + ½, y + ½, −z + ½; #4: x, −y, z + ½; #5: −x + ½, y − ½, −z + ½; #6: x − ½, −y + ½, z − ½.

Example 3

Sensing Properties of Compound 1 Towards DENV and ZIKV RNA Sequences

Detections of RNA sequences were performed by measuring the fluorescence signals of FAM and ROX using fluorescence spectrometry as described before (Yang, S. P. et al., Anal. Chem. 87 (2015) 12206-12214). The fluorescence intensity of FAM at 518 nm with excitation at 480 nm and ROX at 608 nm with excitation at 588 nm was used for quantitative analysis. The fixed wavelength difference (Δλ) of synchronous scanning fluorescence spectroscopy was set at 22 nm. The quenching efficiency $Q_E\%$ was calculated as $Q_E\% = (1 - F_M/F_0) \times 100\%$, wherein $F_M$ and $F_0$ are the fluorescence intensities with and without compound 1, respectively. The fluorescence recovery efficiency $R_E$ was calculated as $R_E = F_T/F_M - 1$, wherein $F_T$ and $F_M$ are the fluorescence intensities with and without the target RNA, respectively.

Figure 3A:
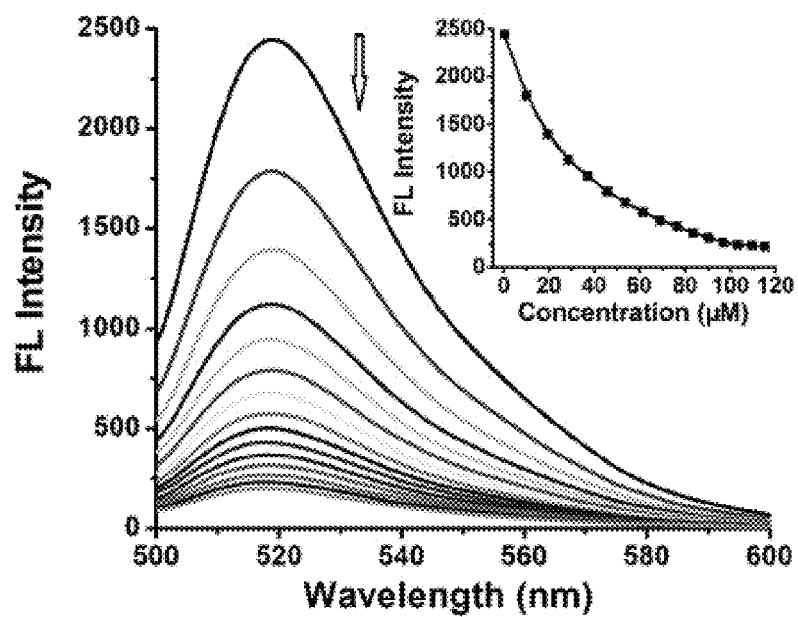
FIGS. 3A and 3B show the fluorescence quenching of the P-DNA-1 and P-DNA-2 incubated with compound 1 of varying concentrations at room temperature. Inset: Plot of fluorescence intensity versus concentrations of compound 1 (concentration of P-DNA=50 nM), wherein FIG. 3A refers to the fluorescence quenching of P-DNA-1 (i.e. DNA of Dengue virus) and FIG. 3B refers to the fluorescence quenching of P-DNA-2 (i.e. DNA of Zika virus).
Figure 3B:
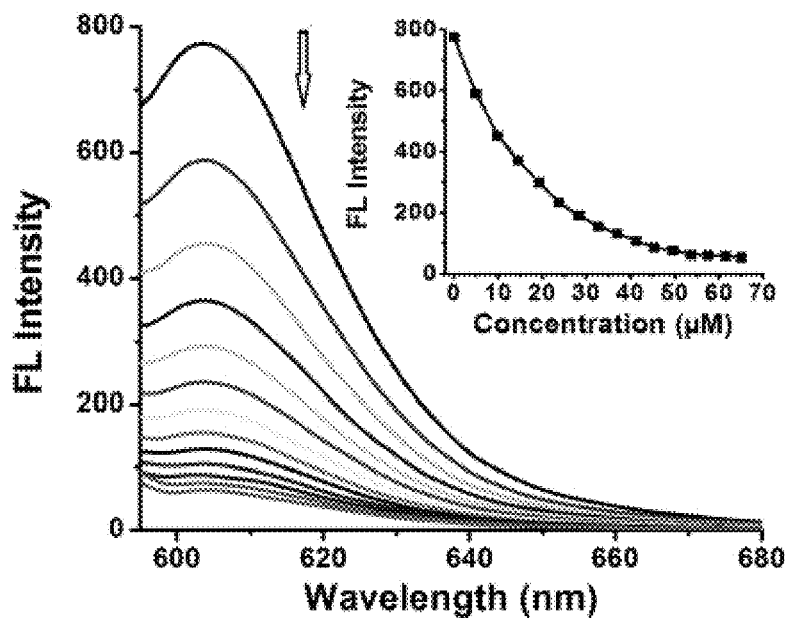
Figure 4A:
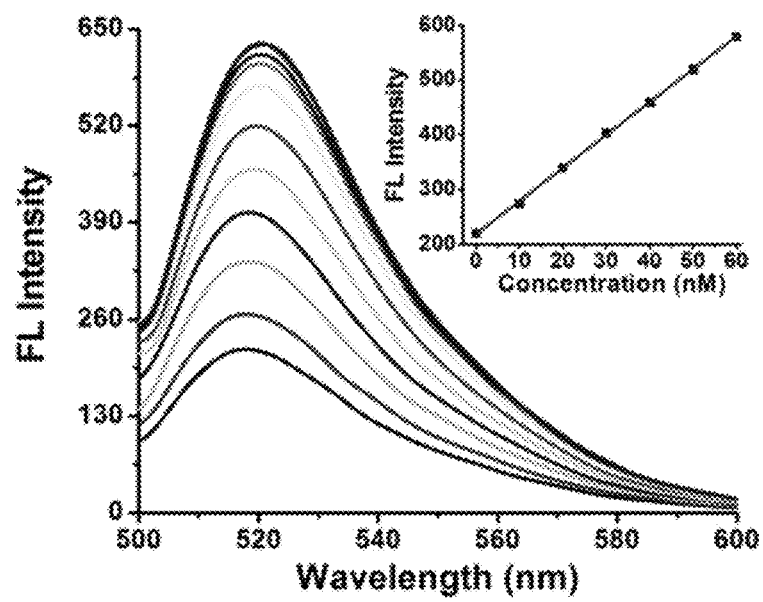
FIGS. 4A and 4B show the fluorescence spectra of the P-DNA-1@1 system (50 nM/100 μM) and P-DNA-2@1 system (50 nM/55 μM) incubated with T$_1$ or T$_2$ of varying concentrations at room temperature. Insets: plots of the fluorescence intensity versus the concentrations of T$_1$ and T$_2$.
Figure 4B:
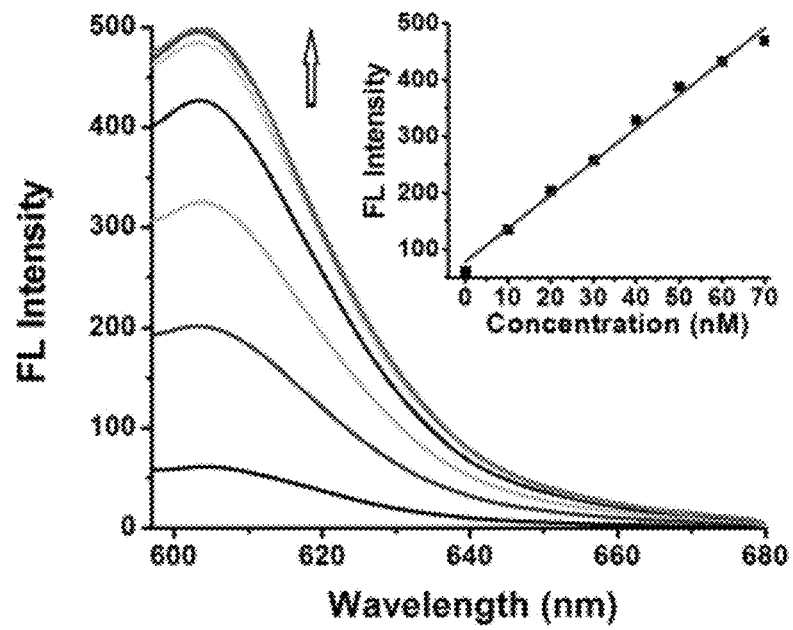
Figure 4C:
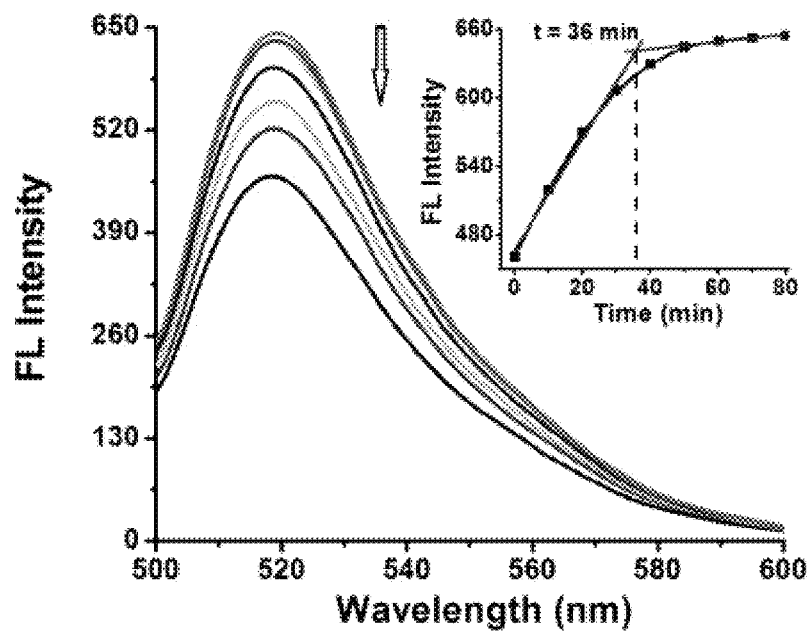
FIGS. 4C and 4D show fluorescence spectra of the P-DNA-1@1 system (50 nM/100 μM) and P-DNA-2@1 system (50 nM/55 μM) in the presence of T$_1$ (25 nM) or T$_2$ (25 nM) at varying incubation time. Insets: plots of the fluorescence intensity versus the incubation time for T$_1$ and T$_2$.
Figure 4D:
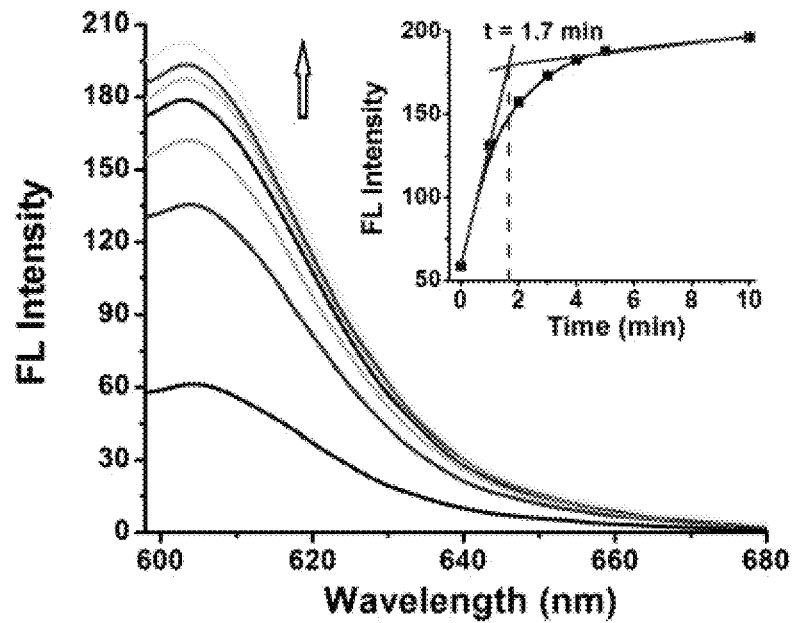

As discussed above, the pores of compound 1 exhibit benzene rings, free carboxylates, positively charged pyridinium and Cu(II) cation centers on the channel surface, which can offer π stacking, electrostatic and/or hydrogen bonding interactions with negatively charged nucleic acids. Firstly, the interaction of compound 1 with two probe single stranded DNAs was studied. The first probe DNA is carboxyfluorescein (FAM)-labeled 5'-FAM-SEQ. ID. NO: 1-3' (P-DNA-1), a complementary sequence of Dengue virus (DENV) RNA. The second one is 5(6)-carboxyrhodamine, triethylammonium salt (ROX)-tagged 5'-ROX- SEQ. ID. NO: 3-3' (P-DNA-2), a complementary sequence of Zika virus (ZIKV) RNA. As shown in FIG. 3A to 3B, the fluorescence intensity of both P-DNAs decreases upon the addition of compound 1. The quenching efficiency ($Q_E\%$) is 92% for both P-DNAs with the saturation concentrations of compound 1 being 100 μM for P-DNA-1 and 55 μM for P-DNA-2, respectively. Thus, compound 1 efficiently quenches the fluorescence of both P-DNAs. Compared with the reported MOFs for the detection of nucleic acids, compound 1 shows relative high quenching efficiency (Table 4). This may be due to that in the channel of compound 1, the rigid ancillary ligand bpe can offer strong π stacking with P-DNAs. On the other hand, free carboxylates can offer hydrogen bonding interactions and positively charged pyridinium and Cu(II) cation centers may offer electrostatic interactions with P-DNAs.

The similar quenching efficiency values for compound 1 toward both P-DNAs may be ascribed to the close binding ability of compound 1 with P-DNA, so the binding interactions were studied using the fluorescence spectra. Compound 1 interacts with P-DNAs through π stacking, electrostatic and hydrogen bonding interactions indicating a static quenching procedure. Therefore, the apparent binding constants ($K_b$) was calculated through the double logarithm equation $\log(F_0-F)/F = n \log[1] + \log K_b$, wherein $F_0$ and F are the fluorescence intensities at 518 nm or 608 nm in the absence and presence of compound 1, $K_b$ is the binding constant and n is the number of binding sites. The values of $K_b$ between compound 1 and P-DNAs were $1.96 \times 10^4$ M$^{-1}$ (P-DNA-1) and $2.938 \times 10^4$ M$^{-1}$ (P-DNA-2), and the number of binding sites per DNA (n) were 1.24 and 1.36, respectively.

TABLE 4

Comparison of performances of fluorescent sensors using MOFs

| MOFs | Structure | Target | $Q_E\%$ | Detection time | Detection limit | Remarks |
|---|---|---|---|---|---|---|
| Compound 1 | 3D | DENV RNA | 92% | 36 min | 332 pM | water-soluble |
| Compound 1 | 3D | ZIKV RNA | 92% | 2 min | 192 pM | water-soluble |
| [Cu$_3$(Cmdcp)$_2$(dps)$_4$(H$_2$O)$_4$(SO$_4$)]$_n$ (Yang, S. P. et al., Anal. Chem. 87 (2015) 12206-12214) | 3D | HIV ds-DNA | 65% | 90 min | 196 pM | water-soluble |
| [Cu$_3$(Cmdcp)$_2$(dps)$_4$(H$_2$O)$_4$(SO$_4$)]$_n$ (Yang, S. P. et al., Anal. Chem. 87 (2015) 12206-12214) | 3D | SUDV RNA | 76% | 30 min | 73 pM | water-soluble |
| {[Dy(Cmdcp)(H$_2$O)$_3$](NO$_3$)$_2$H$_2$O}$_n$ (Qin, L. et al., Chem. Commun. 52 (2016) 132-135) | 3D | SUDN RNA | 60% | 120 min | 160 pM | water-soluble |
| {[Zn(HCbdcp)$_2$]•H$_2$O}$_n$ (Zhao, H. Q. et al., Anal. Chim. Acta. 922 (2016) 55-63) | 2D | HIV ds-DNA | 73% | 80 min | 10 pM | water-soluble |

TABLE 4-continued

Comparison of performances of fluorescent sensors using MOFs

| MOFs | Structure | Target | $Q_E$ % | Detection time | Detection limit | Remarks |
|---|---|---|---|---|---|---|
| Cu(H$_2$dtoa) (Zhu, X. et al., Chem. Commun. 49 (2013) 1276-1278) | 2D | HIV-1 U5 DNA | 85% | 4 h | 3 nM | suspension |
| Cu(H$_2$dtoa) (Zhu, X. et al., Chem. Commun. 49 (2013) 1276-1278) | 2D | thrombin | 85% | 4 h | 1.3 nM | suspension |
| Cu(H$_2$dtoa) (Chen, L. F. et al., Analyst 138 (2013) 3490-3493) | 2D | HIV-1 dsDNA | 81% | 180 min | 1.3 nM | suspension |
| Cu(H$_2$dtoa) (Wei, X. F. et al., J. Mater. Chem. B 1 (2013) 1812-1817) | 2D | H$_5$N$_1$ antibody | 50% | 60 min | 1.6 pM | suspension |
| MIL-101 (Guo, J. F. et al., Rsc Advances 4 (2014) 9379-9382) | 3D | HIV-1 ssDNA | N.A | 50 min | 200 pM | water-stable |
| MIL-101 (Fang, J. M. et al., Analyst 139 (2014) 801-806) | 3D | HIV-1 ssDNA | 89% | 42 min | 73 pM | water-stable |
| MIL-88B (Tian, J. Q. et al., Biosens. Bioelectron. 71 (2015) 1-6) | 3D | HIV-1 ssDNA | ~100% | 4 min | 10 pM | suspension |
| UIO-66-NH$_2$ (Zhang, H. T. et al., Chem. Commun. 50 (2014) 12069-12072) | 3D | HIV-1 ssDNA | 56% | 3 min | / | suspension |
| UiO-66 (Wu, Y. F. et al., Nanoscale 7 (2015) 1753-1759) | 3D | microRNA | 82% | 1.5~3 h | 10 pM | suspension |
| Cd-MOF (Wang, G. Y. et al., J. Mater. Chem. A 2 (2014) 2213-2220) | 3D | Random DNA | 92% | 30 min | 50 pM | suspension |
| Zn-MOF (Wang, G. Y. et al., J. Mater. Chem. A 2 (2014) 2213-2220) | 3D | Random DNA | 97% | 30 min | 50 pM | suspension |

In principle, addition of the complementary target RNA sequences to the P-DNA@1 system may form a stable DNA/RNA hybrid duplex with P-DNA (Zhu, X. et al., Chem. Commun. 49 (2013) 1276-127). The formation of DNA/RNA hybrid duplex compels the P-DNAs away from the surface of compound 1, thereby leading to the fluorescence recovery. Thus, the formed P-DNA@1 systems can serve as sensing platform for the target complementary RNA via the fluorescence recovery profile. Herein, the fluorescence recovery of the sensor for target RNA sequences of DENV (T$_1$) and ZIKV (T$_2$) was explored. As shown in FIG. 4, the fluorescence intensity increased with the concentration of T$_1$ and T$_2$, indicating that the fluorescence recovery was highly dependent on the concentration of the target RNA. The effect of incubation time on the fluorescence intensity was investigated in that incubated time can influence the rate of hybridization reaction between P-DNA probes and their target RNA. The fluorescence intensity increased with incubation time and remained unaltered after 36 min for T$_1$ and 1.7 min for T$_2$. This time-dependence is indicative of a thermodynamically controlled process for hybridization reaction. Thus, 36 min incubation time for T$_1$ detection and 1.7 min incubation time for T$_2$ detection were chosen as the operational conditions. Under this condition, the fluorescence intensity shows good linear relationship with the concentration of T$_1$ in the range of 1-60 nM and T$_2$ in the range of 0.5-70 nM, giving the detection limits of 332 μM for T$_1$ and 192 μM for T$_2$ (S/N=3), respectively. Furthermore, compared with P-DNA, the fluorescence intensity did not return to the previous level after the addition of sufficient target RNA to P-DNA@1 system. This may due to that compound 1 has a certain interaction with the formed P-DNA@RNA hybrid duplex. In order to confirm this possibility, the binding interactions of compound 1 with P-DNA@T$_1$ and P-DNA@T$_2$ were also studied. The apparent binding constants (K$_b$) between compound 1 and P-DNA@T were 2.36×10$^3$ M$^{-1}$ (P-DNA@T$_1$) and 2.57×10$^3$ M$^{-1}$ (P-DNA@T$_2$), respectively. This indicates that the interaction between compound 1 and P-DNAQRNA hybrid duplex exists, leading to the incomplete recovery of the fluorescence intensity.

Synchronous Detection of DENV and ZIKV RNA Sequences

Figure 5:
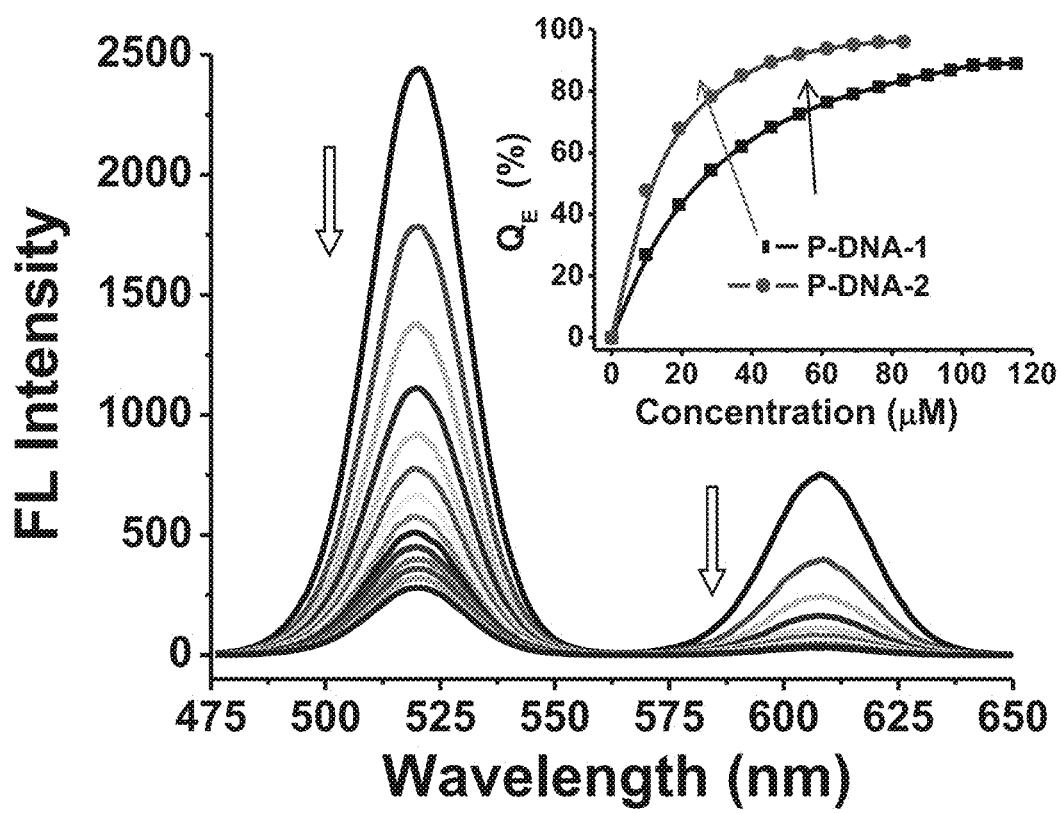
FIG. 5 shows the fluorescence quenching of the P-DNAs (50 nM) incubated with compound 1 of varying concentrations at room temperature. Inset: Plot of fluorescence quenching efficiency (QE %) versus concentrations of compound 1.

Through investigating the changes of fluorescence signals for FAM-labeled or ROX-labeled DNA probes in P-DNA@1 systems before and after hybridization with target RNA, the detection of DENV and ZIKV RNA sequences were respectively realized. The fluorescence signals of FAM and ROX can be obtained simultaneously using synchronous scanning fluorescence spectrometry, as the wavelength intervals between their maximum excitation wavelength and maximum emission wavelength are close (23 and 20 nm). Thus, the simultaneous detections of target RNA sequences of DENV and ZIKV can be realized by measuring synchronous fluorescence signals of FAM and ROX. On the other hand, synchronous fluorescence analysis for multiple nucleic acids can reduce the repeated procedure of sample preparation so as to shorten the analytical time. According the above-mentioned result, the concentration of compound 1 could influence the fluorescence quenching efficiency toward two fluorophore-labeled DNA probes. Therefore, the relationship between the concentration of compound 1 and synchronous fluorescence signals of two fluorophore-labeled DNA probes were investigated as shown in FIG. 5. The results show that the fluorescence intensities of FAM and ROX decreased quickly with increased concentration of compound 1 from 0-80 μM and 0-40 μM respectively, and then tended to level off. The maximal quenching efficiencies were about 82% for FAM and 92% for ROX, respectively. Considering the sensitivity of the assay, 40 μM of compound 1 was selected for the following experiments.

Figure 6:
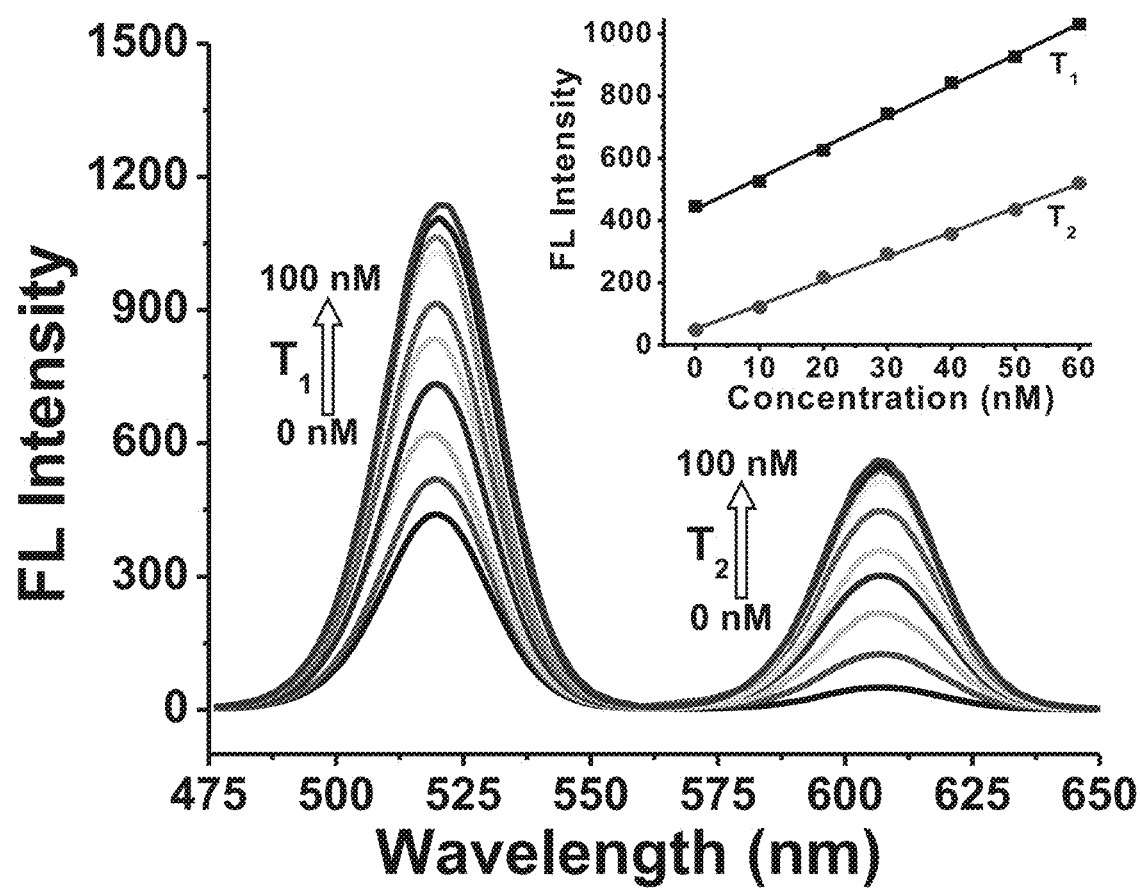
FIG. 6 shows the fluorescence curves of the P-DNAs@1 after incubation with varying concentrations of T$_1$ and T$_2$ at room temperature, P-DNA-1 and P-DNA-2: 50 nM, compound 1: 40 μM. Inset: The linear curve of fluorescence intensity of P-DNAs@1 at 518 nm and 608 nm versus concentrations of T$_1$ and T$_2$, respectively.

When the target RNA sequence of DENV or ZIKV was added to the P-DNAs@1 system, the fluorescence regeneration occurred due to the formation of a stable DNA@RNA hybrid duplex. The synchronous fluorescence spectra of the multiplexed probes upon the addition of different concentrations of target RNA sequences were recorded by synchronous scanning fluorescence spectrometry. As shown in FIG. 6, the fluorescence intensity of P-DNAs@1 increased with the concentration of $T_1$ and $T_2$. Under the optimum conditions, the fluorescence intensities of the two probes all exhibit good linear dependence on their targets RNA concentration in the range of 0-60 nm. For $T_1$, the fitted regression equation is $FL=9.919C_{T1-DENV}+436.5$ with a correlation coefficient of 0.9982 ($R^2$), and that of $T_2$ is $FL=7.779C_{T2-ZIKV}+51.05$ with a correlation coefficient of 0.9981 ($R^2$). The detection limit (3σ, where σ is the standard deviation of a blank solution, n=9) of $T_1$ is estimated to be 184 μM and that of $T_2$ is 121 μM, respectively. Three parallel measurements of 25 nM $T_1$ and $T_2$ is used for estimating the precision and the relative standard deviation (RSD) of $T_1$ is 0.61%, and that of $T_2$ is 0.51%. Compared with single detection of DENV and ZIKV RNA sequences, the detection limit of simultaneous detection is reduced by nearly one fold for DENV RNA sequences and 60% for ZIKV RNA sequences. This shows that synchronous fluorescence analysis for multiple nucleic acids can not only obtain simultaneously multiplexed fluorescence signals and shorten the analytical time, but also reduce the detection limit. The possible reason is that synchronous fluorescence analysis can avoid the interference of Raleigh light scattering signal to the fluorescence signal of fluorophore and improves the detection sensitivity (Ye, T. et al., Analyst 139 (2014) 1721-1725).

Figure 7A:
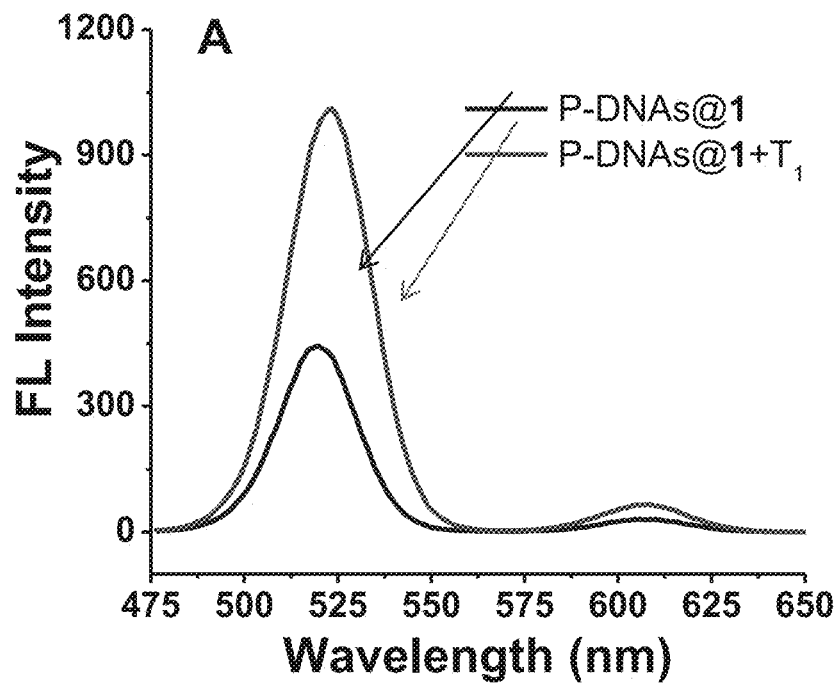
Figure 7B:
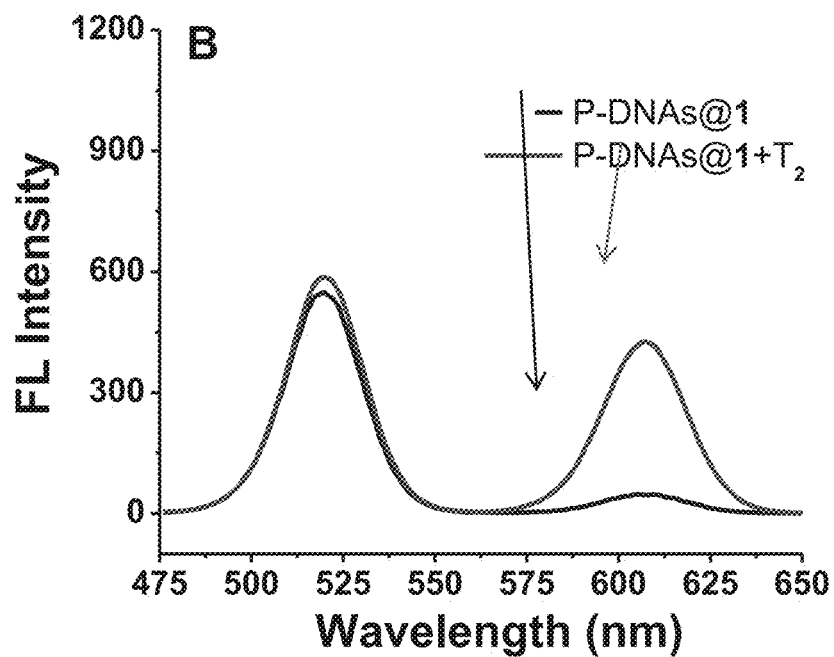
Figure 7C:
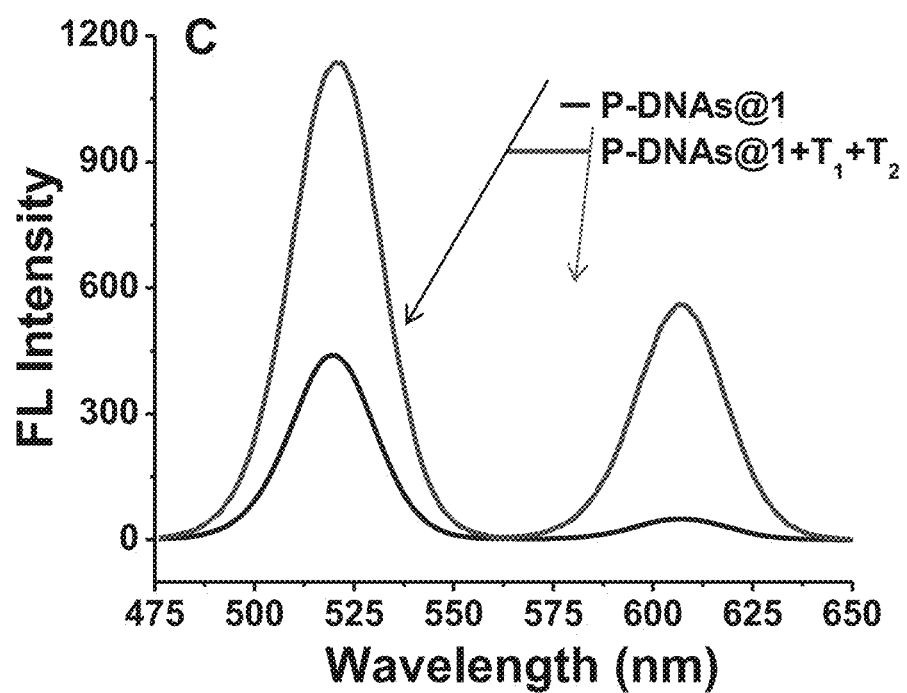

Because the detection system contains two fluorophore-labeled DNA probes, it is necessary to demonstrate whether there is cross reaction between P-DNA-1 and P-DNA-2 for simultaneous detection of $T_1$ and $T_2$, as the cross-reaction is a crucial analytical parameter regarding the assay specificity and thus the reliability of the multiplex detection. As shown in FIG. 7, when $T_1$ alone exists in the sample solution, increased fluorescence intensity of P-DNA-1 was observed. In contrast, when $T_2$ alone exists in the analysis sample, only P-DNA-2 fluorescence intensity increased. When both targets existed in the sample solution, the two distinguishing probe fluorescence intensity increased at the same time. The fluctuation of fluorescence intensity between single detection and simultaneous detection might be due to 80 μM of compound 1 being an overdose for single detection. Consequently, this detection system indicates the potential for applications in multiplexed RNA detection.

To ensure the practical application of P-DNA@1 systems, their sensing ability should not be interfered by other RNA sequences. Therefore, six RNA sequences, including one base pair mutated complementary RNA sequences $T_1'$ and $T_2'$, non-specific RNA sequences $T_A$ for DENV and $T_B$ for ZIKV, specific RNA sequences $T_C$ and $T_D$ of closely related Flavivirus, were chosen to hybridize with P-DNAs in the P-DNAs@1 system. The results indicated that the introduction of complementary target RNA $T_1$ and $T_2$ results in significant fluorescence enhancement with the recovery efficiency ($R_E$) of FAM reaching 1.61 and ROX reaching 10.5. Under the same conditions, the $R_E$ of FAM and ROX are only 0.42 and 0.71 for $T_1'$, 0.26 and 0.93 for $T_2'$, 0.34 and 0.50 for $T_A$, 0.29 and 0.47 for $T_B$, 0.38 and 0.51 for $T_C$, 0.35 and 0.45 for $T_D$ respectively. These results convincingly suggest that P-DNAs@1 systems function as highly selective sensing platforms for the synchronous detection of Dengue and Zika virus RNA sequences in vitro.

The invention claimed is:

1. A method of preparing a crystalline copper-based coordination polymer, that method comprises steps of:
   (i) preparing a mixture comprising copper ions and a first pyridyl ligand which first pyridyl ligand is a quaternized carboxylate pyridyl ligand having a structure of Formula (IV):

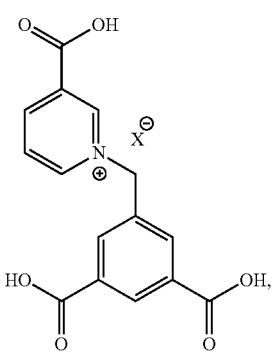

Formula (IV)

with X being a halogen:
   (ii) adding a second pyridyl ligand, which second pyridyl ligand is a polypyridyl ligand having a structure of Formula (V):

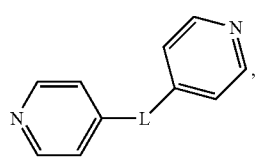

Formula (V)

with L being a linking group selected from —(CH$_2$)$_{n'}$—, —(CH=CH)$_{n'}$— or —(N=N)$_{n'}$— and with n' being an integer and selected from 0, 1, 2 or 3;
   (iii) subjecting the mixture of step (ii) to conditions under which crystals of the copper-based coordination polymer are formed;
   (iv) separating the crystals of the copper-based coordination polymer from the mixture.

2. The method of claim 1, wherein X is Br.

3. The method of claim 1, wherein the second pyridyl ligand has a structure of Formula (VI):

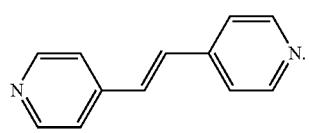

Formula (VI)

4. The method of claim 1, wherein the first pyridyl ligand has a structure of Formula (IV):

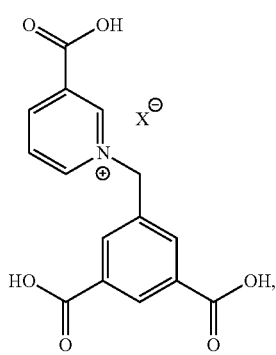

Formula (IV)

with X being Br and the second pyridyl ligand has a structure of formula (VI):

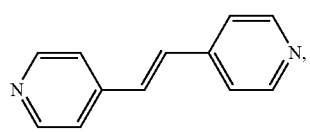

Formula (VI)

and wherein the copper is of the oxidation state +2.

5. The method of claim 1, wherein step (i) comprises steps of:
   a) preparing a first pre-mixture comprising mixing the first pyridyl ligand and a solvent;
   b) preparing a second pre-mixture comprising mixing a copper salt and a solvent;
   c) adding the second pre-mixture to the first pre-mixture;
   d) stirring the mixture at a temperature of about 20° C. to about 30° C. for at least about 10 min.

6. The method of claim 5, wherein the copper salt is a hydrate of CuSO$_4$ and wherein both of the solvent in step a) and the solvent in step b) independently comprise water.

7. The method of claim 6, wherein the first pyridyl ligand, the copper salt and the second pyridyl ligand are used in a molar ratio of about 1:1:1.

8. The method of claim 1, wherein step (iii) of subjecting the mixture of step (ii) to conditions under which crystals of the copper-based coordination polymer are formed in particular includes steps of:
   a) stirring the mixture at a temperature of about 20° C. to about 30° C.;
   b) filtering the mixture for obtaining a filtrate and a residue;
   c) heating the filtrate to a temperature of at least about 80° C. for at least about 30 min;
   d) allowing the filtrate to stand at a temperature of at least about 80° C. for at least about 48 h;
   e) allowing the mixture after step d) to cool down to a temperature of about 25° C. to about 35° C. for at least about 24 h.

9. The method of claim 1, wherein step (iv) comprises steps of:
   a) separating the crystals from the mixture;
   b) purifying the crystals;
   c) drying the crystals.

10. The method of claim 1, wherein adding a second pyridyl ligand in step (ii) is carried out by adding a mixture of the second pyridyl ligand in a solvent with solvent comprises dimethylformamide.

11. A crystalline copper-based coordination polymer obtained by a method for preparing it comprising:
    (i) preparing a mixture comprising copper ions and a first pyridyl ligand which first pyridyl ligand is a quaternized carboxylate pyridyl ligand having a structure of Formula IV):

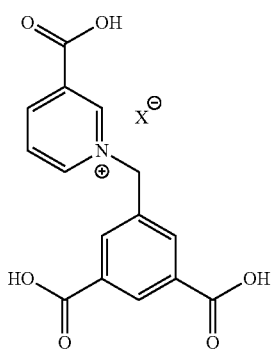

Formula (IV)

with X being a halogen;

(ii) adding a second pyridyl ligand, which second pyridyl ligand is a polypyridyl ligand having a structure of Formula (V):

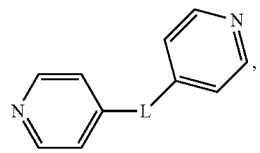

Formula (V)

with L being a linking group selected from —(CH$_2$)$_{n'}$—, —(CH═CH)$_{n'}$— or —(N═N)$_{n'}$— and with n' being an integer and selected from 0, 1, 2 or 3;

(iii) subjecting the mixture of step (ii) to conditions under which crystals of the copper-based coordination polymer are formed;

(iv) separating the crystals of the copper-based coordination polymer from the mixture.

12. The crystalline copper-based coordination polymer of claim 11, wherein the pyridyl ligand in step (i) has a structure of Formula (IV):

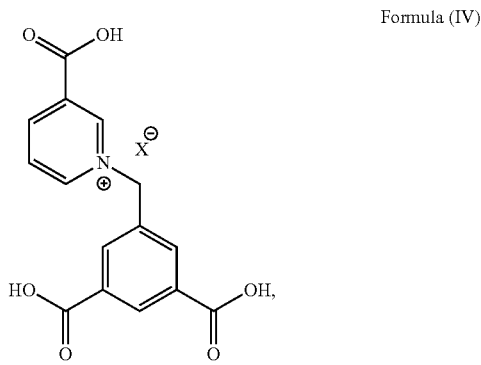

Formula (IV)

with X being Br and wherein the second pyridyl ligand has a structure of formula (VI):

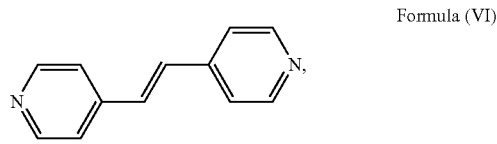 [SMILES: C(=C\c1ccncc1)/c1ccncc1]

Formula (VI)

and the copper is of the oxidation state +2.

13. A method of detecting at least a first target nucleic acid sequence in a sample comprising:
    (i) preparing a mixture of a crystalline copper-based coordination polymer of claim 11 and at least a first oligonucleotide probe having a nucleic acid sequence at least partially complementary to the first target nucleic acid sequence and being labeled with a fluorescent;
    (ii) incubating the mixture with the sample;
    (iii) measuring the fluorescence after step (ii);
    (iv) determining the presence and/or amount of the target nucleic acid sequence in the sample based on the fluorescence in step (iii).

14. The method of claim 13, wherein the crystalline copper-based coordination polymer is of claim 12.

15. The method of claim 13, wherein the at least first oligonucleotide probe is a FAM-labeled ss-DNA sequence of SEQ. ID. NO: 1 and the at least first target nucleic acid sequence comprises SEQ. ID. NO: 2.

16. The method of claim 13, wherein the at least first oligonucleotide probe is a ROX-labeled ss-DNA sequence of SEQ. ID. NO: 3 and the at least first target nucleic acid sequence comprises SEQ. ID. NO: 4.

17. The method of claim 13, wherein the method is for detecting a first and a second target nucleic acid sequence in the sample, which first target nucleic acid comprises SEQ. ID. NO: 2 and which second nucleic acid sequence comprises SEQ. ID. NO:4, wherein in step (i) a first and a second oligonucleotide probe is used, the first being a FAM-labeled ss-DNA sequence of SEQ. ID. NO: 1 and the second being a ROX-labeled ss-DNA sequence of SEQ. ID. NO: 3.

* * * * *